(12) United States Patent
Wardle et al.

(10) Patent No.: US 8,663,150 B2
(45) Date of Patent: Mar. 4, 2014

(54) DELIVERING OCULAR IMPLANTS INTO THE EYE

(75) Inventors: John Wardle, San Clemente, CA (US); Andrew T. Schieber, Irvine, CA (US)

(73) Assignee: Ivantis, Inc., Irvine, CA (US)

( * ) Notice: Subject to any disclaimer, the term of this patent is extended or adjusted under 35 U.S.C. 154(b) by 0 days.

(21) Appl. No.: 13/330,592

(22) Filed: Dec. 19, 2011

(65) Prior Publication Data

US 2013/0158462 A1   Jun. 20, 2013

(51) Int. Cl.
*A61F 9/007* (2006.01)
*A61M 5/00* (2006.01)

(52) U.S. Cl.
USPC .................. 604/8; 604/9; 606/107; 606/108

(58) Field of Classification Search
USPC ......... 604/8, 9; 606/107, 108; 623/1.11–1.12, 623/1.23; 600/184–190
See application file for complete search history.

(56) References Cited

U.S. PATENT DOCUMENTS

| | | | |
|---|---|---|---|
| 3,788,327 | A | 1/1974 | Donowitz et al. |
| 3,811,442 | A | 5/1974 | Maroth |
| 3,948,271 | A | 4/1976 | Akiyama |
| 4,037,604 | A | 7/1977 | Newkirk |
| 4,428,746 | A | 1/1984 | Mendez |
| 4,457,757 | A | 7/1984 | Molteno |
| 4,722,724 | A | 2/1988 | Schocket |
| 4,733,665 | A | 3/1988 | Palmaz |
| 4,750,901 | A | 6/1988 | Molteno |
| 4,826,478 | A | 5/1989 | Schocket |
| 4,886,488 | A | 12/1989 | White |
| 4,934,809 | A | 6/1990 | Volk |
| 4,936,825 | A | 6/1990 | Ungerleider |
| 4,946,436 | A | 8/1990 | Smith |
| 4,968,296 | A | 11/1990 | Ritch et al. |

(Continued)

FOREIGN PATENT DOCUMENTS

| | | |
|---|---|---|
| AU | 1998/76197 B2 | 2/1999 |
| CN | 1950091 A | 4/2007 |

(Continued)

OTHER PUBLICATIONS

Lynch, Mary G.; U.S. Appl. No. 60/131,030 entitled "Devices and methods for treating glaucoma by enhancing aqueous outflow through schlemm's canal and anterior chamber angle," filed Apr. 26, 1999.

(Continued)

*Primary Examiner* — Philip R Wiest
*Assistant Examiner* — Ariana Zimbouski
(74) *Attorney, Agent, or Firm* — Shay Glenn LLP

(57) ABSTRACT

A method of deploying an ocular implant into Schlemm's canal of an eye. The method includes the steps of inserting a distal end of a cannula through a cornea of the eye and into an anterior chamber of the eye, the cannula having a distal opening extending from the distal end and through a side wall; placing the distal opening of the cannula into fluid communication with Schlemm's canal; advancing the ocular implant distally through the cannula with a delivery tool engaged with the ocular implant, a proximal portion of the ocular implant engaging the delivery tool proximal to a distal portion of the delivery tool; and disengaging the ocular implant and the delivery tool when the proximal portion of the ocular implant reaches the cannula distal opening. The invention also includes a system for practicing the method.

10 Claims, 28 Drawing Sheets

(56) References Cited

U.S. PATENT DOCUMENTS

| | | |
|---|---|---|
| 5,092,837 A | 3/1992 | Ritch et al. |
| 5,127,901 A | 7/1992 | Odrich |
| 5,178,604 A | 1/1993 | Baerveldt et al. |
| 5,180,362 A | 1/1993 | Worst |
| 5,213,569 A | 5/1993 | Davis |
| 5,246,452 A | 9/1993 | Sinnott |
| 5,360,399 A | 11/1994 | Stegmann |
| 5,372,577 A | 12/1994 | Ungerleider |
| 5,454,796 A | 10/1995 | Krupin |
| 5,458,615 A | 10/1995 | Klemm et al. |
| 5,591,223 A | 1/1997 | Lock et al. |
| 5,626,558 A | 5/1997 | Suson |
| 5,792,099 A | 8/1998 | DeCamp et al. |
| 5,807,302 A | 9/1998 | Wandel |
| 5,865,831 A | 2/1999 | Cozean et al. |
| 5,868,697 A | 2/1999 | Richter et al. |
| 5,879,319 A | 3/1999 | Pynson et al. |
| 5,893,837 A | 4/1999 | Eagles et al. |
| 5,948,427 A | 9/1999 | Yamamoto et al. |
| 5,968,058 A | 10/1999 | Richter et al. |
| 6,007,511 A | 12/1999 | Prywes |
| 6,050,970 A | 4/2000 | Baerveldt |
| 6,102,045 A | 8/2000 | Nordquist et al. |
| 6,186,974 B1 | 2/2001 | Allan et al. |
| 6,221,078 B1 | 4/2001 | Bylsma |
| 6,238,409 B1 | 5/2001 | Hojeibane |
| D444,874 S | 7/2001 | Haffner et al. |
| 6,375,642 B1 | 4/2002 | Grieshaber et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,094,225 B2 | 8/2006 | Tu et al. |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 * | 9/2011 | Karageozian ............ 604/8 |
| 8,034,105 B2 | 10/2011 | Stegmann et al. |
| 8,123,729 B2 | 2/2012 | Yamamoto et al. |
| 8,308,701 B2 | 11/2012 | Horvath et al. |
| 2001/0002438 A1 | 5/2001 | Sepetka et al. |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0072673 A1 | 6/2002 | Yamamoto et al. |
| 2002/0133168 A1 | 9/2002 | Smedley et al. |
| 2002/0143284 A1 | 10/2002 | Tu et al. |
| 2003/0004457 A1 | 1/2003 | Andersson |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0093084 A1 | 5/2003 | Nissan et al. |
| 2003/0097151 A1 | 5/2003 | Smedley et al. |
| 2003/0181848 A1 | 9/2003 | Bergheim et al. |
| 2003/0187384 A1 | 10/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0082939 A1 | 4/2004 | Berlin |
| 2004/0088048 A1 | 5/2004 | Richter et al. |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0249333 A1 | 12/2004 | Bergheim et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0244464 A1 | 11/2005 | Hughes |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0106370 A1 | 5/2006 | Baerveldt et al. |
| 2006/0116626 A1 | 6/2006 | Smedley et al. |
| 2006/0149194 A1 | 7/2006 | Conston et al. |
| 2006/0154981 A1 | 7/2006 | Klimko et al. |
| 2006/0155238 A1 | 7/2006 | Shields |

(56) References Cited

U.S. PATENT DOCUMENTS

| | | |
|---|---|---|
| 2006/0155300 A1 | 7/2006 | Stamper et al. |
| 2006/0173397 A1 | 8/2006 | Tu et al. |
| 2006/0178674 A1 | 8/2006 | McIntyre |
| 2006/0189915 A1 | 8/2006 | Camras et al. |
| 2006/0189916 A1 | 8/2006 | Bas |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0241749 A1 | 10/2006 | Tu et al. |
| 2007/0010827 A1 | 1/2007 | Tu et al. |
| 2007/0027452 A1 | 2/2007 | Varner et al. |
| 2007/0073275 A1 | 3/2007 | Conston et al. |
| 2007/0088432 A1 | 4/2007 | Solovay et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0179520 A1 | 8/2007 | West |
| 2007/0191863 A1 | 8/2007 | De Juan, Jr. et al. |
| 2007/0202186 A1 | 8/2007 | Yamamoto et al. |
| 2007/0265582 A1* | 11/2007 | Kaplan et al. ............ 604/260 |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0298068 A1 | 12/2007 | Badawi et al. |
| 2008/0015488 A1 | 1/2008 | Tu et al. |
| 2008/0045878 A1 | 2/2008 | Bergheim et al. |
| 2008/0058704 A1 | 3/2008 | Hee et al. |
| 2008/0228127 A1* | 9/2008 | Burns et al. ............ 604/9 |
| 2009/0005852 A1* | 1/2009 | Gittings et al. ............ 623/1.11 |
| 2009/0028953 A1 | 1/2009 | Yamamoto et al. |
| 2009/0030363 A1 | 1/2009 | Gellman |
| 2009/0030381 A1 | 1/2009 | Lind et al. |
| 2009/0043321 A1 | 2/2009 | Conston et al. |
| 2009/0069786 A1 | 3/2009 | Vesely et al. |
| 2009/0082860 A1 | 3/2009 | Schieber et al. |
| 2009/0082862 A1 | 3/2009 | Schieber et al. |
| 2009/0104248 A1 | 4/2009 | Rapacki et al. |
| 2009/0132040 A1 | 5/2009 | Frion et al. |
| 2009/0138081 A1 | 5/2009 | Bergheim et al. |
| 2009/0182421 A1 | 7/2009 | Silvestrini et al. |
| 2009/0227934 A1 | 9/2009 | Euteneuer et al. |
| 2009/0247955 A1 | 10/2009 | Yamamoto et al. |
| 2009/0281520 A1* | 11/2009 | Highley et al. ............ 604/506 |
| 2010/0004580 A1 | 1/2010 | Lynch et al. |
| 2010/0057072 A1 | 3/2010 | Roman et al. |
| 2010/0121342 A1 | 5/2010 | Schieber et al. |
| 2010/0137981 A1 | 6/2010 | Silvestrini et al. |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0222733 A1 | 9/2010 | Schieber et al. |
| 2010/0234726 A1 | 9/2010 | Sirimanne et al. |
| 2010/0234790 A1 | 9/2010 | Tu et al. |
| 2011/0009874 A1 | 1/2011 | Wardle et al. |
| 2011/0009958 A1 | 1/2011 | Wardle et al. |
| 2011/0098809 A1 | 4/2011 | Wardle et al. |
| 2011/0196487 A1 | 8/2011 | Badawi et al. |
| 2011/0218523 A1 | 9/2011 | Robl |
| 2011/0319806 A1 | 12/2011 | Wardle |
| 2012/0010702 A1 | 1/2012 | Stegmann et al. |
| 2012/0022424 A1 | 1/2012 | Yamamoto et al. |
| 2012/0035524 A1 | 2/2012 | Silvestrini |
| 2012/0136439 A1 | 5/2012 | Schieber et al. |
| 2012/0191064 A1 | 7/2012 | Conston et al. |
| 2012/0271272 A1 | 10/2012 | Hammack et al. |
| 2013/0006165 A1 | 1/2013 | Euteneuer et al. |
| 2013/0079701 A1 | 3/2013 | Schieber et al. |
| 2013/0267887 A1 | 10/2013 | Kahook et al. |

FOREIGN PATENT DOCUMENTS

| | | |
|---|---|---|
| DE | 4226476 C1 | 8/1993 |
| DE | 19840047 A1 | 3/2000 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| JP | H10-504978 A | 5/1998 |
| JP | 11123205 | 5/1999 |
| JP | 2006289075 A | 10/2006 |
| WO | WO 00/07525 A1 | 2/2000 |
| WO | WO 00/64389 A1 | 11/2000 |
| WO | WO 00/64393 A1 | 11/2000 |
| WO | WO 01/97727 A1 | 12/2001 |
| WO | WO 02/36052 A1 | 5/2002 |
| WO | WO 02/074052 A2 | 9/2002 |
| WO | WO 02/080811 A2 | 10/2002 |
| WO | WO 03/015659 A2 | 2/2003 |
| WO | WO 03/045290 A1 | 6/2003 |
| WO | WO 2004/054643 A1 | 7/2004 |
| WO | WO 2004/093761 A1 | 11/2004 |
| WO | WO 2005/105197 A2 | 11/2005 |
| WO | WO 2006/066103 A2 | 6/2006 |
| WO | WO 2007/035356 A2 | 3/2007 |
| WO | WO 2007/047744 A2 | 4/2007 |
| WO | WO 2007/087061 A2 | 8/2007 |
| WO | WO 2008/002377 A1 | 1/2008 |
| WO | WO 2008/005873 A2 | 1/2008 |
| WO | WO 2009/120960 A2 | 10/2009 |
| WO | WO 2011/053512 A1 | 5/2011 |
| WO | WO 2011/057283 A1 | 5/2011 |
| WO | WO 2011/106781 A1 | 9/2011 |
| WO | WO 2011/150045 A1 | 12/2011 |
| WO | WO 2012/051575 A2 | 4/2012 |

OTHER PUBLICATIONS

Bahler, et al.; Trabecular bypass stents decrease intraocular pressure in cultured human anterior segments; Amer. Journal of Ophthalmology; vol. 138, No. 6; pp. 988-994.e2; Dec. 2004.

D'Ermo, et al.; Our results with the operation of ab externo trabeculotomy; Ophthalmologica; vol. 163; pp. 347-355; Feb. 1971.

Ellingsen et al.; Trabeculotomy and sinusotomy in enucleated human eyes; Investigative Ophthalmology; vol. 11; pp. 21-28; Jan. 1972.

Grant; Experimental aqueous perfusion in enucleated human eyes; Archives of Ophthalmology; vol. 69; pp. 783-801; Jun. 1963.

Johnstone et al.; "Microsurgery of Schlemm's Canal and the Human Aqueous Outflow System;" American Journal of Ophthalmology, vol. 76 (6): 906-917; Dec. 1973.

Lee et al.; Aqueous-venous shunt and intraocular pressure. Preliminary report of animal studies; Investigative Ophthalmology; vol. 5; No. 1; pp. 59-64; Feb. 1966.

Moses, Robert; The effect of intraocular pressure on resistance to outflow; Survey of Ophthalmology; vol. 22; No. 2; pp. 88-100; Sep.-Oct. 1977.

Mäepea et al.; The pressures in the episcleral veins, schlemm's canal and the trabecular meshwork in monkeys: effects of changes in intraocular pressure; Exp. Eye Res.; vol. 49; pp. 645-663; Oct. 1989.

Rosenquist et al.; Outflow resistance of enucleated human eyes at two different perfusion pressures and different extents of trabeculotomy; Current Eye Res.; vol. 8; No. 12; pp. 1233-1240; Dec. 1989.

Savage, James; Gonioscopy in the management of glaucoma; Am. Academy of Ophthalmology; Focal Points; vol. XXIV; No. 3; pp. 1-14; Mar. 2006.

Schultz, Jared; Canaloplasty procedure shows promise for open-angle glaucoma in European study; Ocular Surgery News; vol. 34; Mar. 1, 2007.

Smit et al.; Effects of viscoelastic injection into schlemm's canal in primate and human eyes; J. Am. Academy of Ophthalmology; vol. 109; No. 4; pp. 786-792; Apr. 20002.

Spiegel et al.; Schlemm's canal implant: a new method to lower intraocular pressure in patients with POAG?; Ophthalmic Surgery and Lasers; vol. 30; No. 6; pp. 492-494; Jun. 1999.

(56) References Cited

OTHER PUBLICATIONS

Wardle et al.; U.S. Appl. No. 13/160,355 entitled "Ocular implants for delivery into the eye," filed Jun. 14, 2011.

Schieber et al.; U.S. Appl. No. 13/425,874 entitled "Glaucoma Treatment Method," filed Mar. 21, 2012.

Schieber et al.; U.S. Appl. No. 13/763,394 entitled "Ocular Implant Architectures," filed Feb. 8, 2013.

Schieber et al.; U.S. Appl. No. 13/776,592 entitled "Glaucoma Treatment Method," filed Feb. 25, 2013.

Wardle et al.; U.S. Appl. No. 13/744,351 entitled "Suspended goniolens system," filed Jan. 17, 2013.

Wardle et al.; U.S. Appl. No. 13/793,638 entitled "Ocular Implants for Delivery into an Anterior Chamber of the Eye," filed Mar. 11, 2013.

* cited by examiner

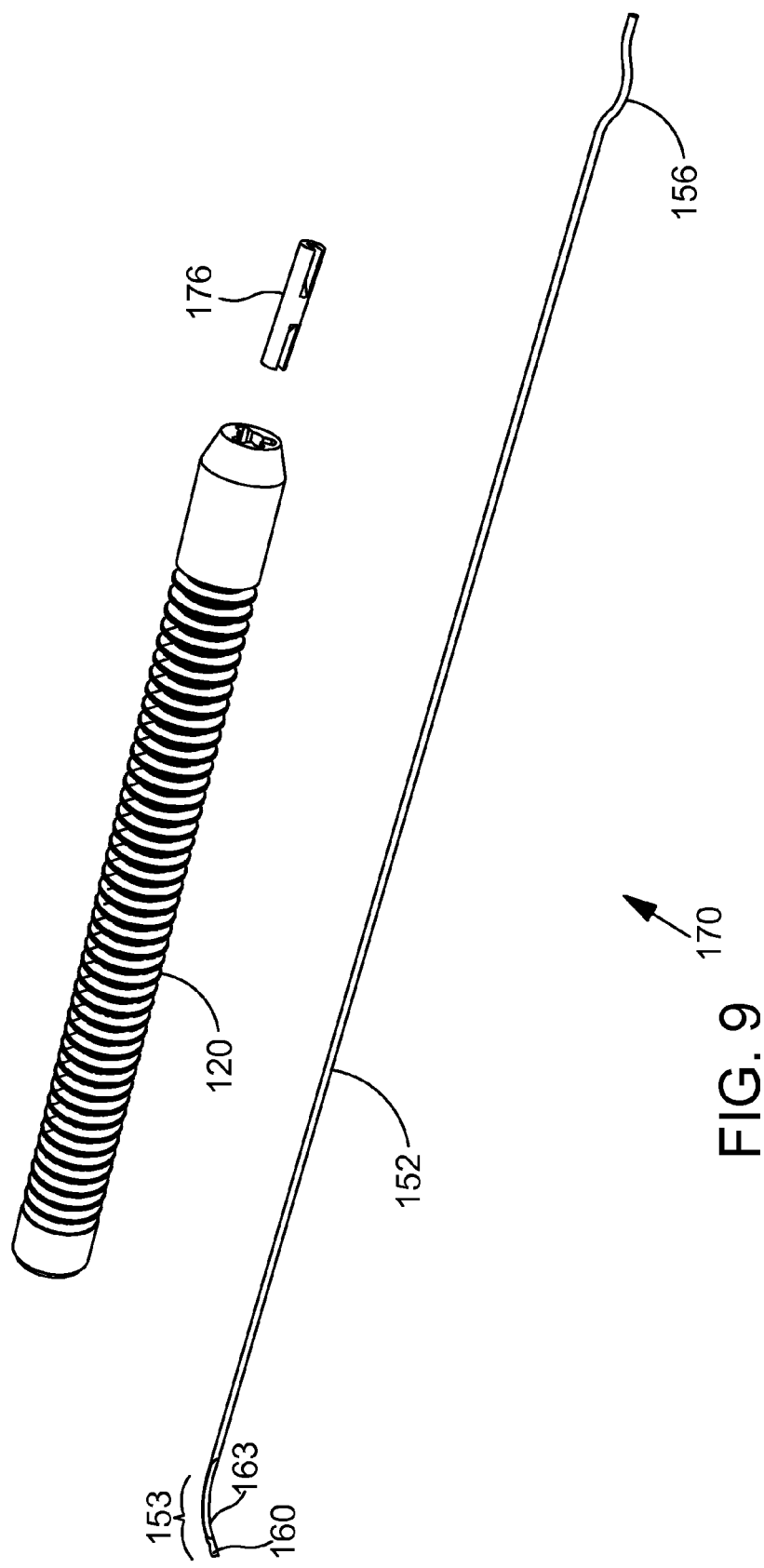

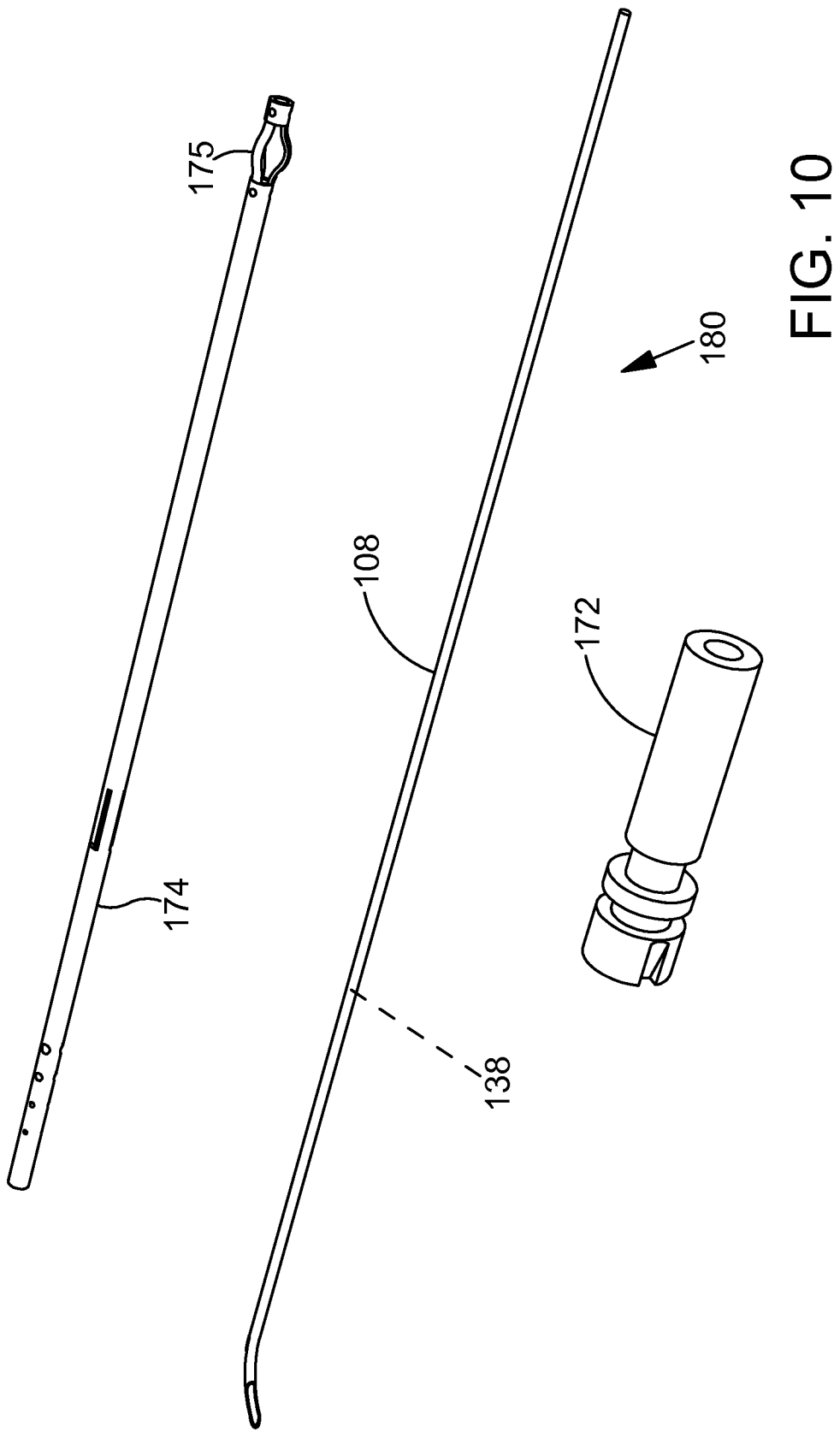

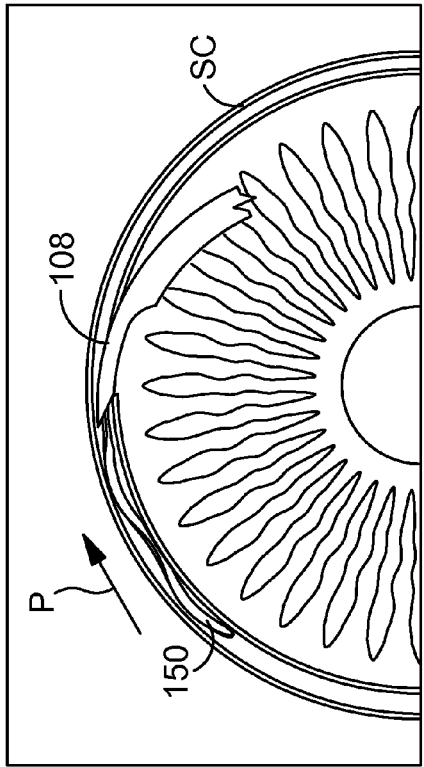
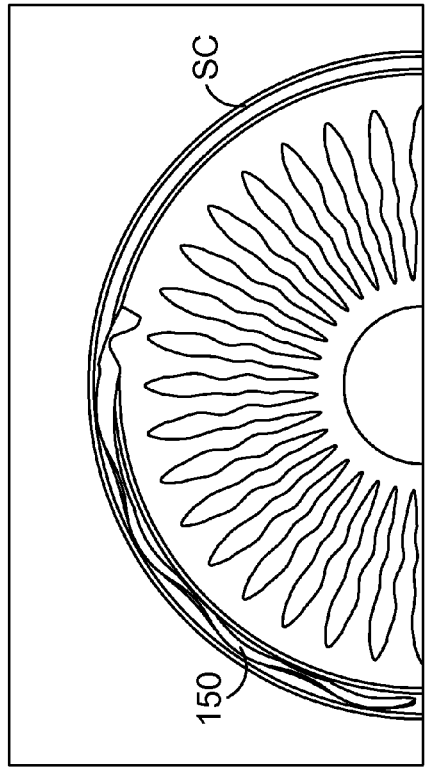
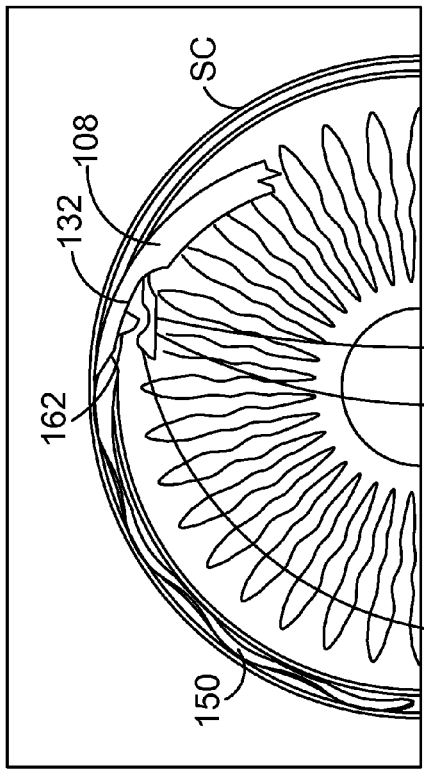
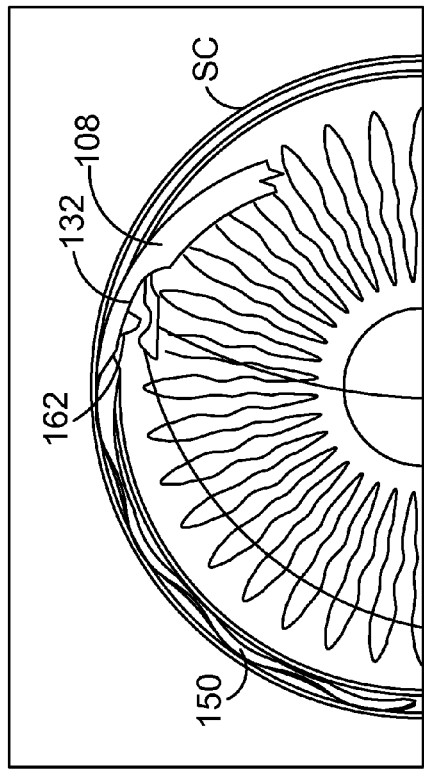

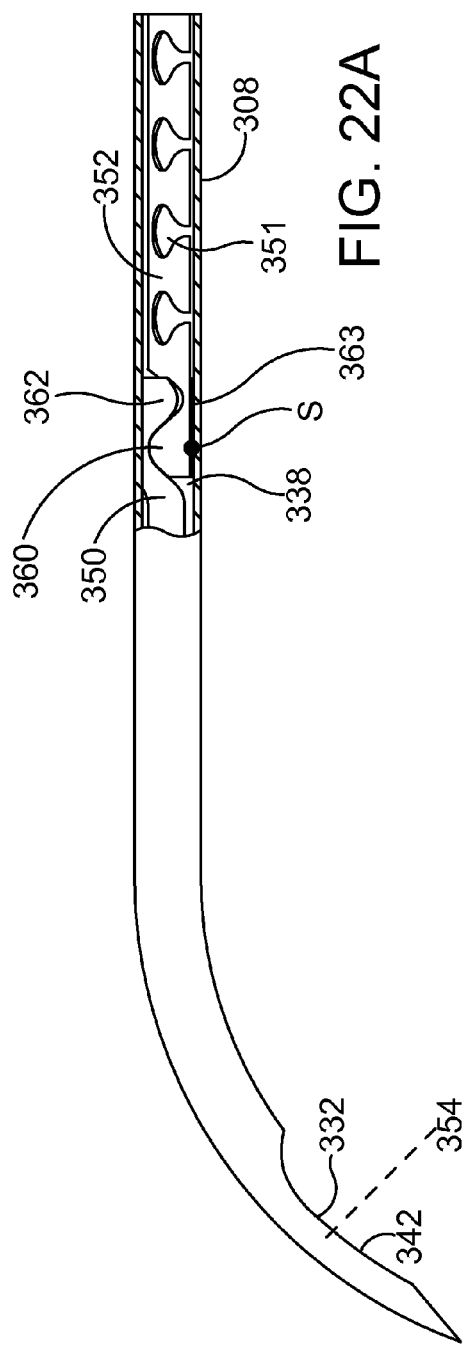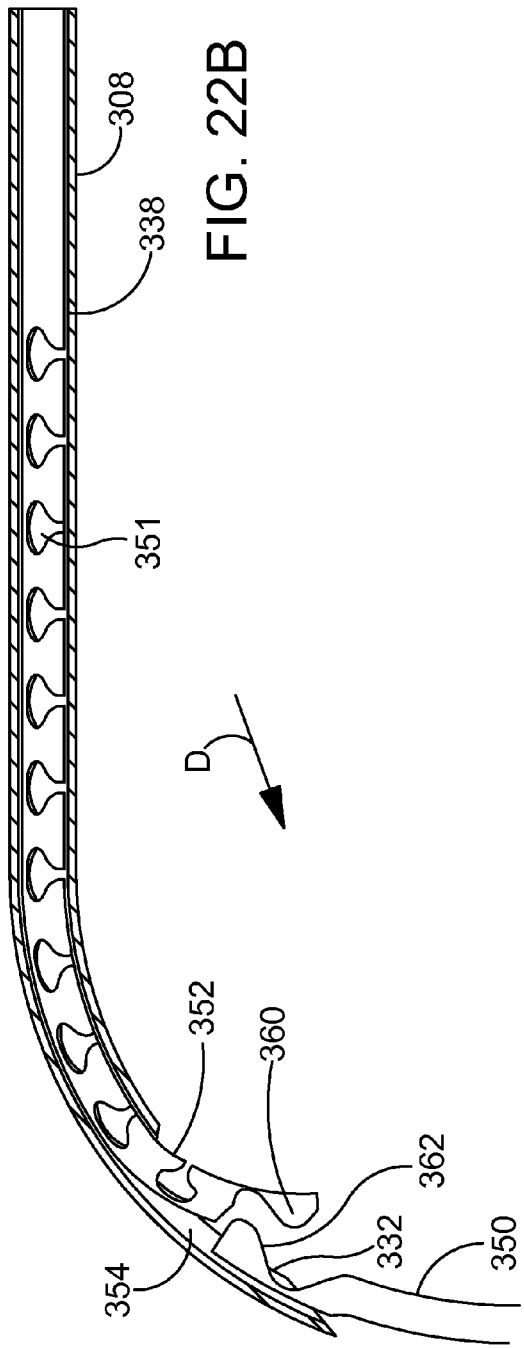

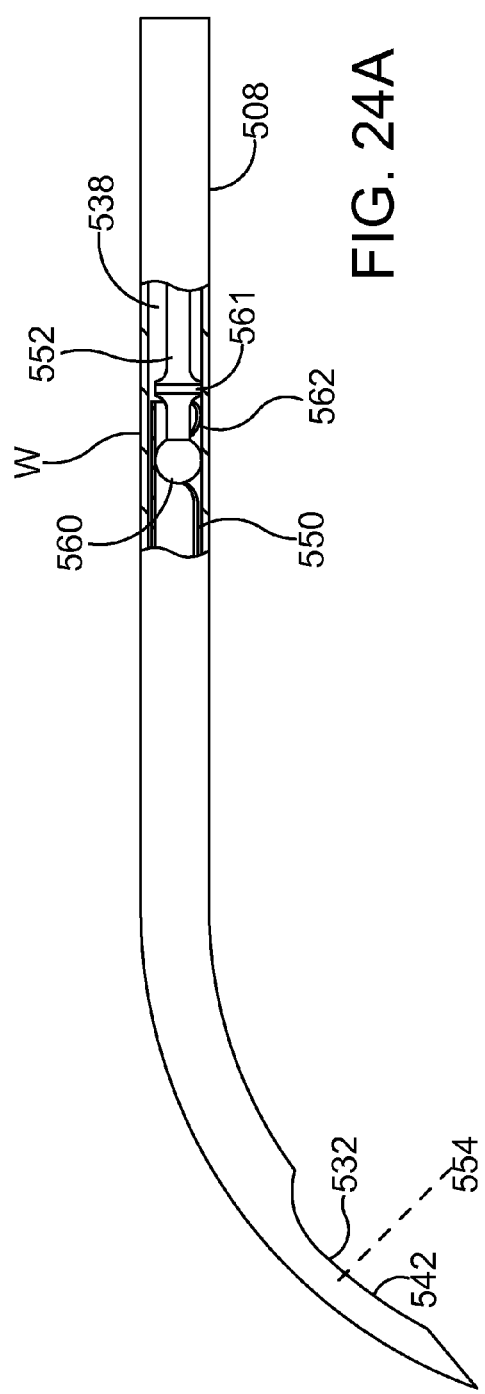
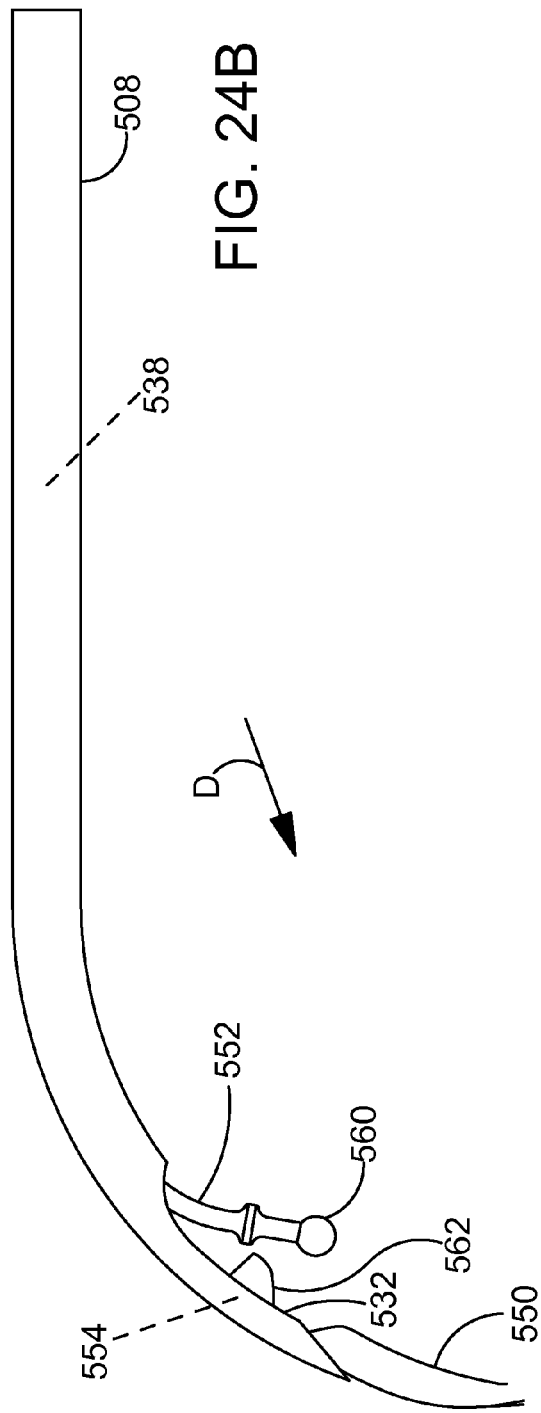

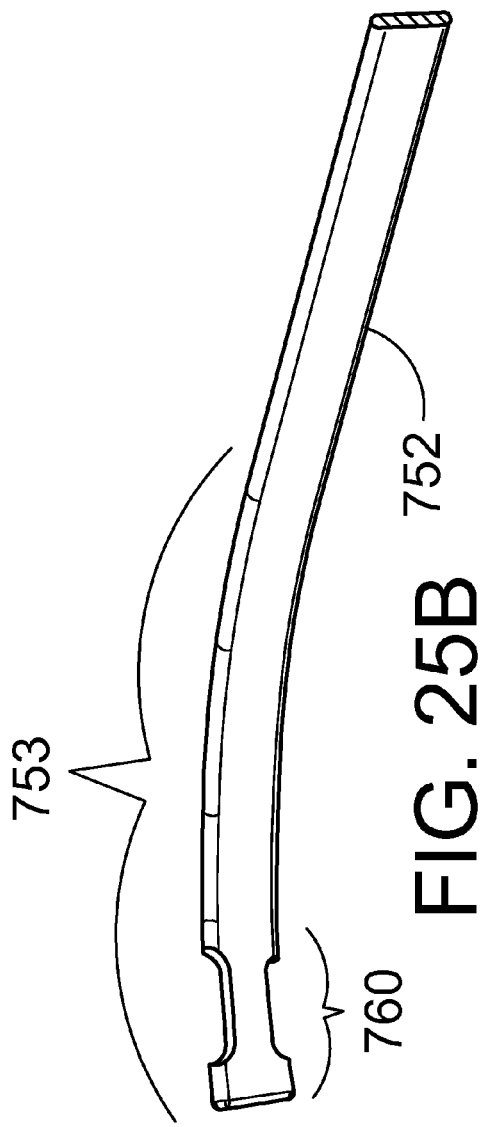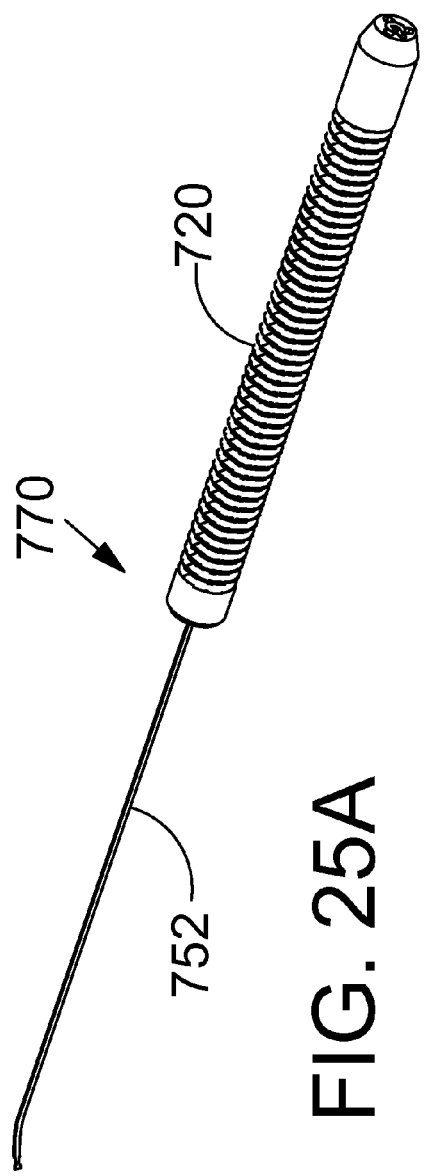
FIG. 25B
FIG. 25A

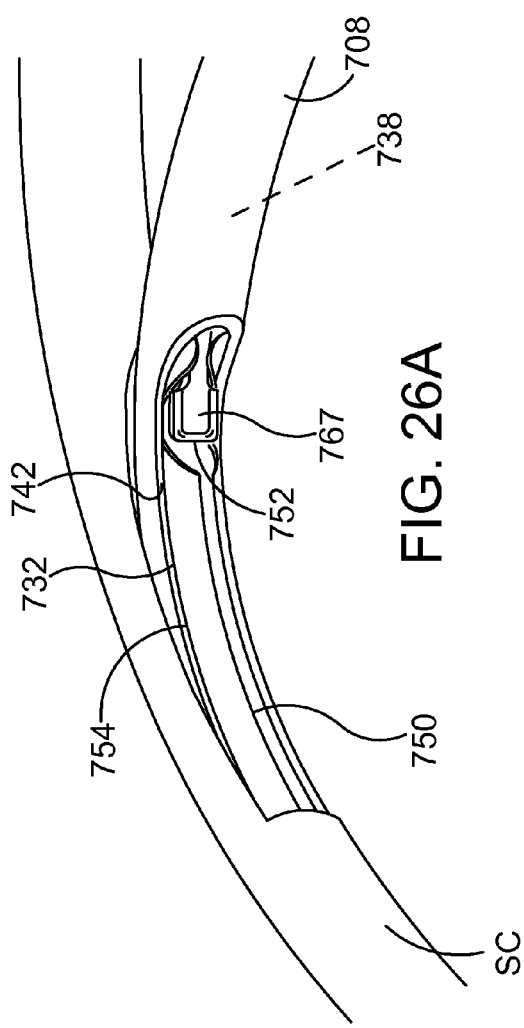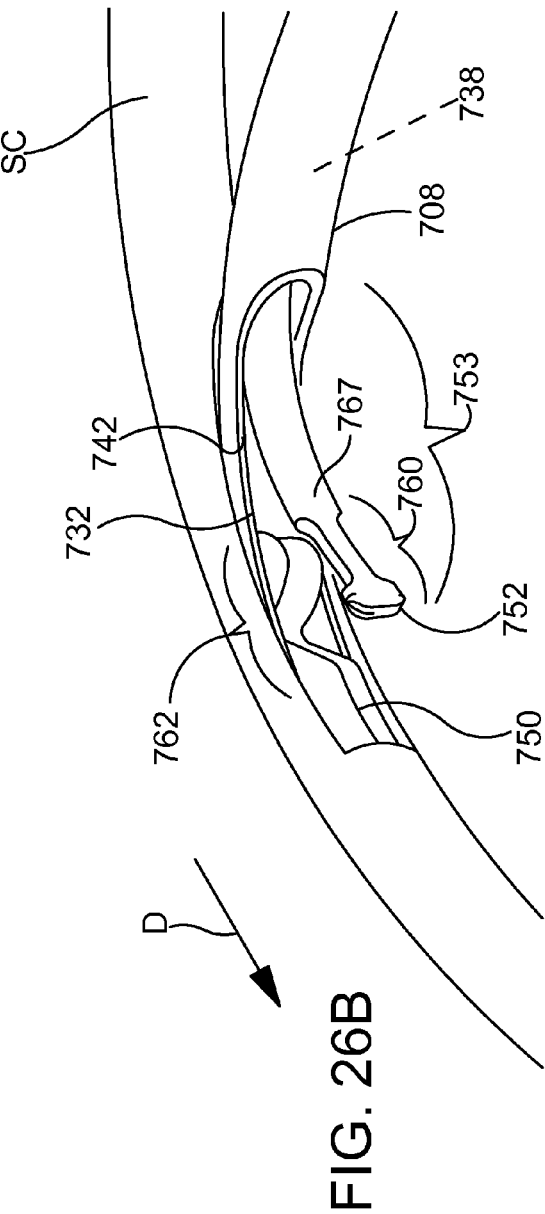

DELIVERING OCULAR IMPLANTS INTO THE EYE

FIELD OF THE INVENTION

The present invention relates generally to the medical devices and treatments for the eye. More particularly, the present invention relates to systems, devices and methods for delivering ocular implants into the eye for treating glaucoma.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid known as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," Investigative Ophthalmology (February 1966)). Other early glaucoma treatment implants led from the anterior chamber to a subconjunctival bleb (e.g., U.S. Pat. Nos. 4,968,296 and 5,180,362). Still others were shunts leading from the anterior chamber to a point just inside Schlemm's canal (Spiegel et al., "Schlemm's canal implant: a new method to lower intraocular pressure in patients with POAG?" Ophthalmic Surgery and Lasers (June 1999); U.S. Pat. Nos. 6,450,984; 6,450,984).

SUMMARY OF THE DISCLOSURE

One aspect of the invention provides a method of deploying an ocular implant into Schlemm's canal of an eye. In some embodiments, the method includes the steps of inserting a distal end of a cannula through a cornea of the eye and into an anterior chamber of the eye, the cannula having a distal opening extending from the distal end and through a side wall; placing the distal opening of the cannula into fluid communication with Schlemm's canal; advancing the ocular implant distally through the cannula with a delivery tool engaged with the ocular implant, a proximal portion of the ocular implant engaging the delivery tool proximal to a distal portion of the delivery tool; and disengaging the ocular implant and the delivery tool when the proximal portion of the ocular implant reaches the cannula distal opening.

In some embodiments, the disengaging step includes the step of separating the distal portion of the delivery tool and the ocular implant from each other when the distal portion of the delivery tool passes through the distal opening of the cannula. In some such embodiments, the separating step is performed before the distal portion of the delivery tool reaches the distal end of the cannula. The separating step may include the step of maintaining contact between the ocular implant and the cannula and moving the distal portion of the delivery tool away from the cannula. In embodiments in which the distal portion of the delivery tool has an at-rest shape (such as, e.g., a curve having a smaller radius of curvature than a distal portion of the cannula), the separating step may also include the step of permitting the distal portion of the delivery tool to assume its at-rest shape.

In some embodiments, the inserting step includes the step of placing the distal end of the cannula in Schlemm's canal and a portion of the cannula distal opening outside of Schlemm's canal, the disengaging step including the step of disengaging the ocular implant and the delivery tool while the proximal portion of the ocular implant is disposed outside of Schlemm's canal. The disengaging step may also include the step of disengaging the ocular implant and the delivery tool while the proximal portion of the ocular implant is disposed inside the anterior chamber of the eye.

Some embodiments include the step of, after the disengaging step: re-engaging the delivery tool and the ocular implant; moving the delivery tool and the ocular implant in a proximal direction to withdraw at least a portion of the ocular implant from Schlemm's canal; advancing the ocular implant and delivery tool distally into Schlemm's canal; and disengaging the ocular implant and the delivery tool.

The method's disengaging step may also include the step of disengaging an interlocking portion of the delivery tool from a complementary interlocking portion of the ocular implant.

Another aspect of the invention provides a system with a cannula having a side wall defining a passageway, the cannula including an opening extending through a distal end and the side wall, the opening fluidly communicating with the passageway; an ocular implant disposed inside the passageway defined by the cannula; a delivery tool having a distal interlocking portion engaging a complementary interlocking portion of the ocular implant to form a mechanically interlocking connection when the interlocking portion of the delivery tool is proximal to the trough portion of the cannula.

In some embodiments, the distal interlocking portion of the delivery tool has an at-rest shape different from the shape of the cannula (such as, e.g., a curve having a smaller radius of curvature than a radius of curvature of the cannula), the cannula side wall preventing the delivery tool from assuming its at-rest shape when the interlocking portion of the delivery tool is proximal to the trough portion of the cannula.

In some embodiments, the system also has a cannula subassembly including the cannula and a delivery tool subassembly including the delivery tool, the delivery tool subassembly and the cannula subassembly engaging one another at a keyed interface, the keyed interface being configured to permit the delivery tool to slide along the passageway defined by the cannula, and the keyed interface being configured to prohibit rotation of the delivery tool subassembly relative to the cannula subassembly so that a predetermined orientation between the delivery tool and the cannula is maintained.

In some embodiments, the delivery tool subassembly includes a rotating rack gear defining a shaped hole having a predetermined shape in lateral cross-section and the cannula subassembly including a shaped portion configured to cooperate with the shaped hole of the rotating rack gear so that the delivery tool is free to slide along the passageway defined by the cannula and rotation of the delivery tool relative to the cannula is prohibited.

In some embodiments, the opening extending through the distal end and the side wall of the cannula is dimensioned and positioned such that, when the ocular implant reaches a predefined location along the passageway, the delivery tool will move toward an undeformed shape in which the interlocking portion of the delivery tool disengages the complementary interlocking portion of the ocular implant to release the ocular implant. The delivery tool may also have a cannula wall engagement surface diametrically opposite the interlocking portion and a reduced diameter portion proximal to the interlocking portion.

In some embodiments, the mechanically interlocking connection is configured to preclude axial and/or movement of the ocular implant relative to the delivery tool. The mechanically interlocking connection may include a peak of the delivery tool that is received in a valley of the ocular implant or a peak of the ocular implant that is received in a valley of the delivery tool.

In some embodiments, the system also includes a motion control mechanism configured to be operated from a location outside of the eye to move the delivery tool and the ocular implant along the passageway defined by the cannula.

BRIEF DESCRIPTION OF THE DRAWINGS

FIG. 9 is an exploded perspective view further illustrating the delivery tool subassembly shown in the exploded perspective view of FIG. 8.

FIG. 10 is an exploded perspective view further illustrating the cannula subassembly shown in the exploded perspective view of FIG. 8.

FIG. 20A-FIG. 20H are a series of stylized plan views illustrating example methods in accordance with the detailed description and associated apparatus used while performing those methods.

FIG. 22A is a stylized plan view further illustrating the delivery tool shown in FIG. 21. FIG. 22B is an additional stylized plan view illustrating the cannula, ocular implant, and delivery tool shown in FIG. 22A.

FIG. 24A is a stylized plan view further illustrating the cannula shown in FIG. 23. FIG. 24B is an additional stylized plan view illustrating the cannula, ocular implant, and delivery tool shown in FIG. 24A.

FIG. 25A is a perspective view showing a delivery tool subassembly that may be part of a delivery system (e.g., the delivery system shown in FIG. 8). FIG. 25B is a perspective view of the distal end of the delivery tool of this embodiment.

FIG. 26A is a stylized perspective view showing a cannula having a distal portion positioned so as to extend through the wall of Schlemm's canal. An ocular implant is shown extending out a distal opening of the cannula and into Schlemm's canal. FIG. 26B is an additional perspective view showing the ocular implant and the cannula shown in FIG. 26A.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figure 1:
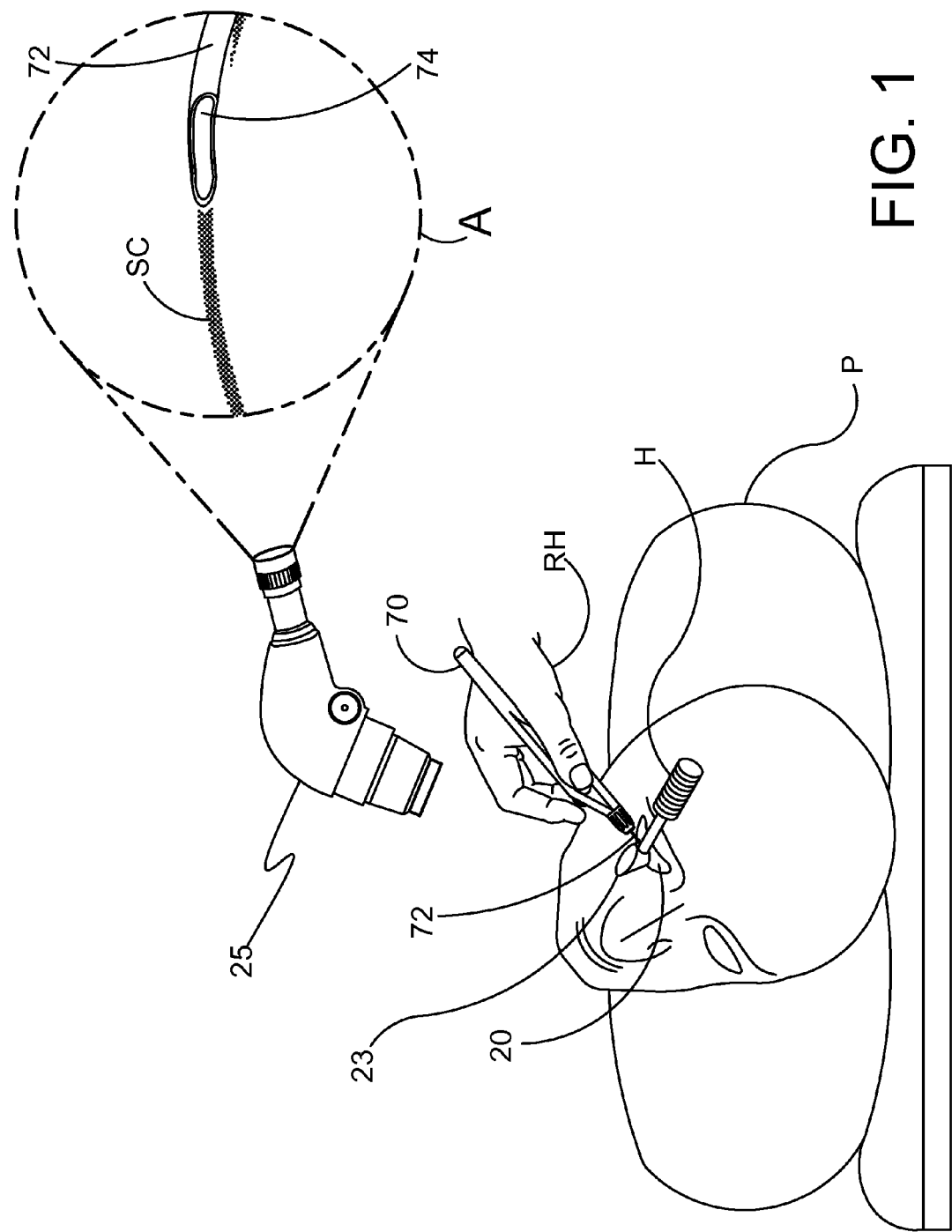
FIG. 1 is a stylized representation of a medical procedure in accordance with this detailed description.

FIG. 1 is a stylized representation of a medical procedure in accordance with this detailed description. In the procedure of FIG. 1, a physician is treating an eye 20 of a patient P. In the procedure of FIG. 1, the physician is holding a hand piece of a delivery system 70 in his or her right hand RH. The physician's left hand (not shown) may be used to hold the handle H of a gonio lens 23. Alternatively, some physicians may prefer holding the delivery system hand piece in the left hand and the gonio lens handle H in the right hand RH.

During the procedure illustrated in FIG. 1, the physician may view the interior of the anterior chamber using gonio lens 23 and a microscope 25. Detail A of FIG. 1 is a stylized simulation of the image viewed by the physician. A distal portion of a cannula 72 is visible in Detail A. A shadow-like line indicates the location of Schlemm's canal SC which is lying under various tissues (e.g., the trabecular meshwork) that surround the anterior chamber. A distal opening 74 of cannula 72 is positioned near Schlemm's canal SC of eye 20.

Methods in accordance with this detailed description may include the step of advancing the distal end of cannula 72 through the cornea of eye 20 so that a distal portion of cannula 72 is disposed in the anterior chamber of the eye. Cannula 72 may then be used to access Schlemm's canal of the eye, for example, by piercing the wall of Schlemm's canal with the distal end of cannula 72. Distal opening 74 of cannula 72 may be placed in fluid communication with a lumen defined by Schlemm's canal. The ocular implant may be advanced out of distal opening 74 and into Schlemm's canal. Insertion of the ocular implant into Schlemm's canal may facilitate the flow of aqueous humor out of the anterior chamber of the eye.

Figure 2:
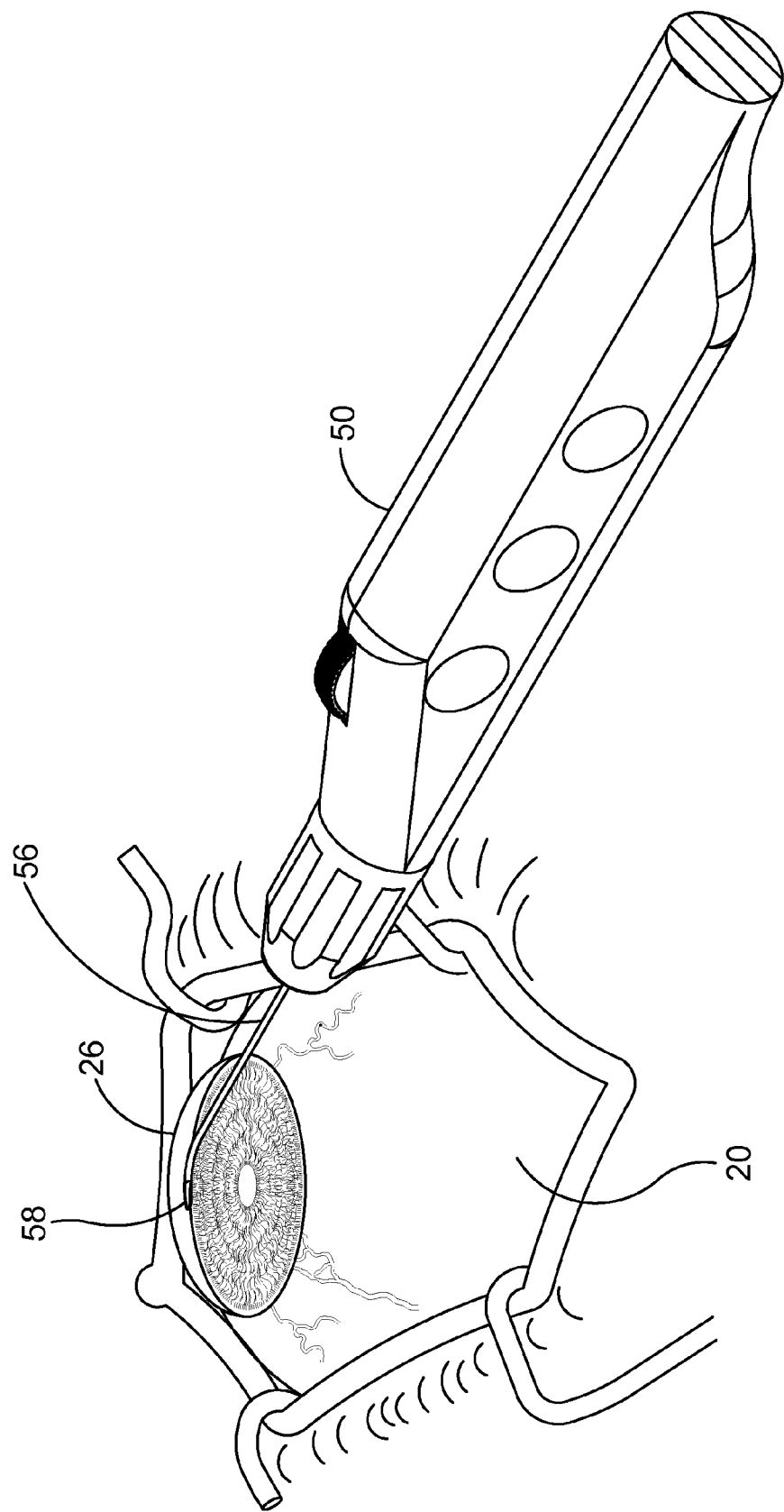
FIG. 2 is an enlarged perspective view further illustrating the delivery system and the eye shown in FIG. 1.

FIG. 2 is an enlarged perspective view further illustrating delivery system 50 and eye 20 shown in the previous figure. In FIG. 2, cannula 56 of delivery system 50 is shown extending through a cornea 26 of eye 20. A distal portion of cannula 56 is disposed inside the anterior chamber defined by cornea 26 of eye 20. In the embodiment of FIG. 2, cannula 56 is configured so that a distal opening 58 of cannula 56 can be placed in fluid communication with Schlemm's canal.

In the embodiment of FIG. 2, an ocular implant is disposed in a passageway defined by cannula 56. Delivery system 50 includes a mechanism that is capable of advancing and retracting the ocular implant along the length of cannula 56. The ocular implant may be placed in Schlemm's canal of eye 20 by advancing the ocular implant through the distal opening of cannula 56 while the distal opening is in fluid communication with Schlemm's canal.

Figure 3:
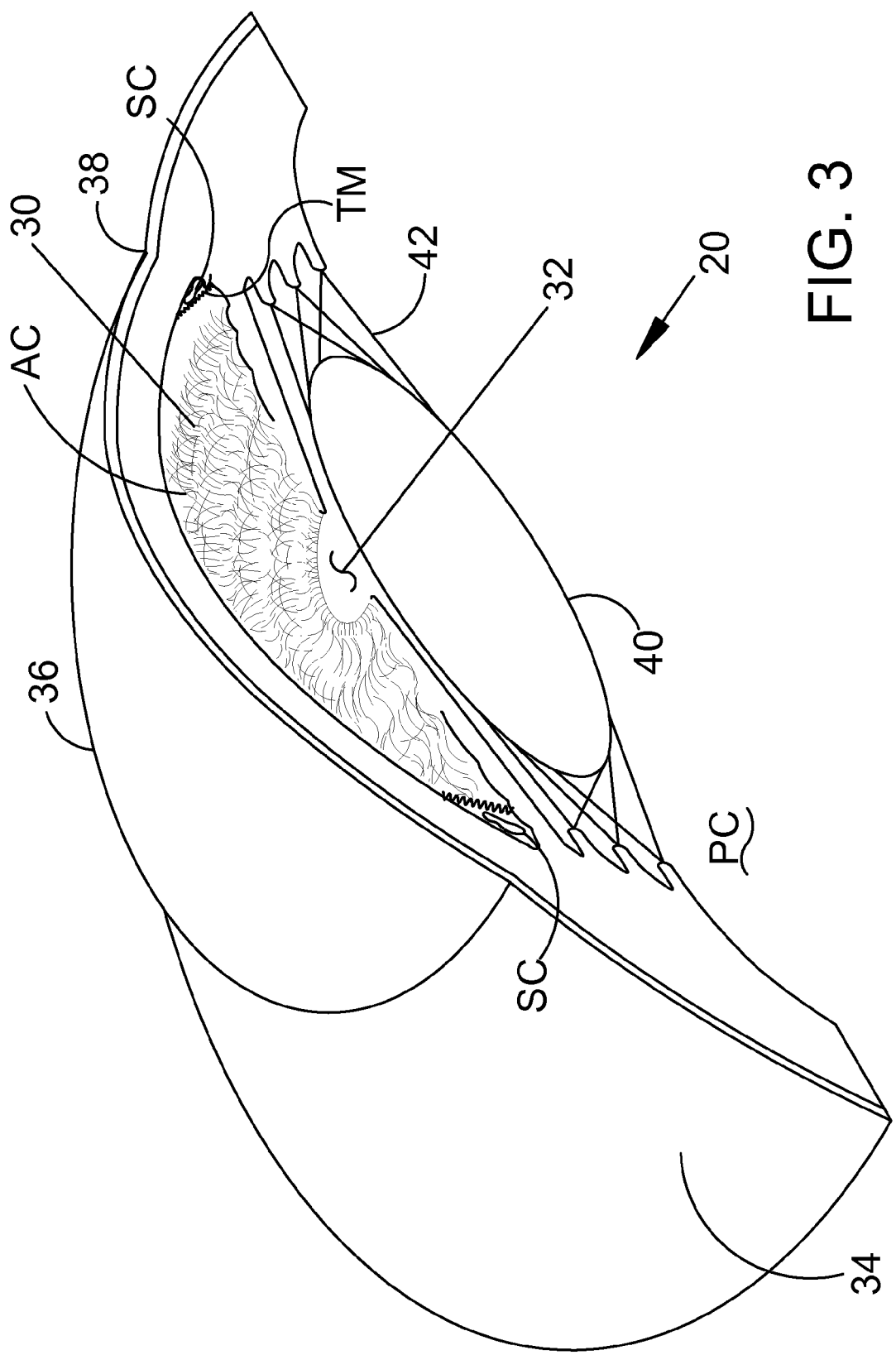
FIG. 3 is a stylized perspective view illustrating the anatomy of an eye.

FIG. 3 is a stylized perspective view illustrating a portion of eye 20 discussed above. Eye 20 includes an iris 30 defining a pupil 32. In FIG. 3, eye 20 is illustrated in a cross-sectional view created by a cutting plane passing through the center of pupil 32. Eye 20 can be conceptualized as a fluid filled ball having two chambers. Sclera 34 of eye 20 surrounds a posterior chamber PC filled with a viscous fluid known as vitreous humor. Cornea 36 of eye 20 encloses an anterior chamber AC that is filled with a fluid known as aqueous humor. The cornea 36 meets the sclera 34 at a limbus 38 of eye 20. A lens 40 of eye 20 is located between anterior chamber AC and posterior chamber PC. Lens 40 is held in place by a number of ciliary zonules 42.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

Schlemm's canal SC is a tube-like structure that encircles iris 30. Two laterally cut ends of Schlemm's canal SC are visible in the cross-sectional view of FIG. 3. In a healthy eye, aqueous humor flows out of anterior chamber AC and into Schlemm's canal SC. Aqueous humor exits Schlemm's canal SC and flows into a number of collector channels. After leaving Schlemm's canal SC, aqueous humor is absorbed into the venous blood stream and carried out of the eye.

Figure 4:
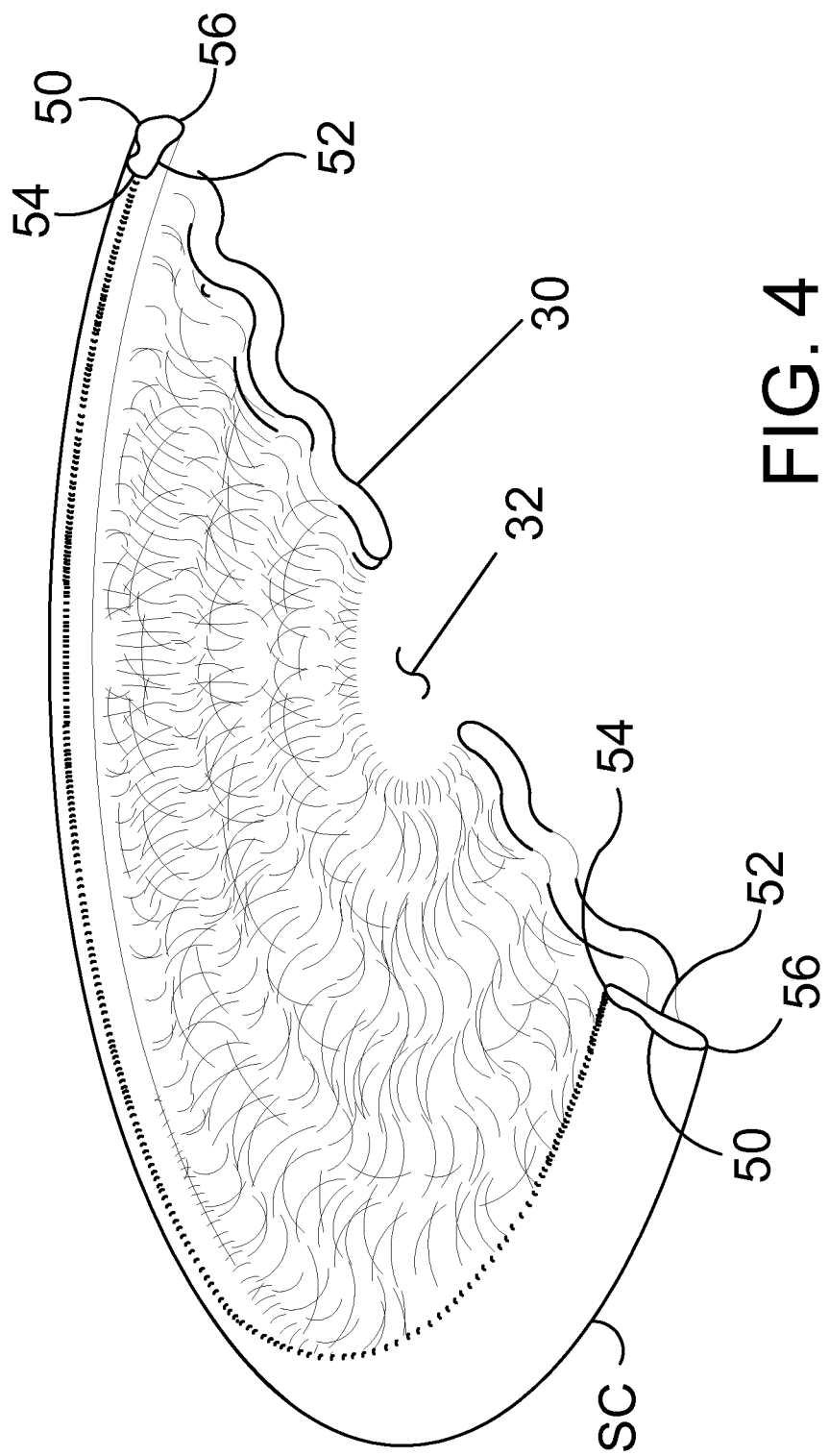
FIG. 4 is a stylized perspective view showing Schlemm's canal and an iris of the eye shown in the previous figure.

FIG. 4 is a stylized perspective view showing Schlemm's canal SC and iris 30 of eye 20 shown in the previous figure. In FIG. 4, Schlemm's canal SC is shown encircling iris 30. With reference to FIG. 4, it will be appreciated that Schlemm's canal SC may overhang iris 30 slightly. Iris 30 defines a pupil 32. In the embodiment of FIG. 4, Schlemm's canal SC and iris 30 are shown in cross-section, with a cutting plane passing through the center of pupil 32.

The shape of Schlemm's canal SC is somewhat irregular, and can vary from patient to patient. The shape of Schlemm's canal SC may be conceptualized as a cylindrical-tube that has been partially flattened. With reference to FIG. 4, it will be appreciated that Schlemm's canal SC has a first major side 50, a second major side 52, a first minor side 54, and a second minor side 56.

Schlemm's canal SC forms a ring around iris 30 with pupil 32 disposed in the center of that ring. With reference to FIG. 4, it will be appreciated that first major side 50 is on the outside of the ring formed by Schlemm's canal SC and second major side 52 is on the inside of the ring formed by Schlemm's canal SC. Accordingly, first major side 50 may be referred to as an outer major side of Schlemm's canal SC and second major side 52 may be referred to as an inner major side of Schlemm's canal SC. With reference to FIG. 4, it will be appreciated that first major side 50 is further from pupil 32 than second major side 52. The outer major wall of Schlemm's canal is supported by scleral tissue of the eye. Elevated pressure inside the eye of a patient suffering from glaucoma may cause the inside major wall of Schlemm's canal to be pressed against the outer major wall of the canal.

Figure 5:
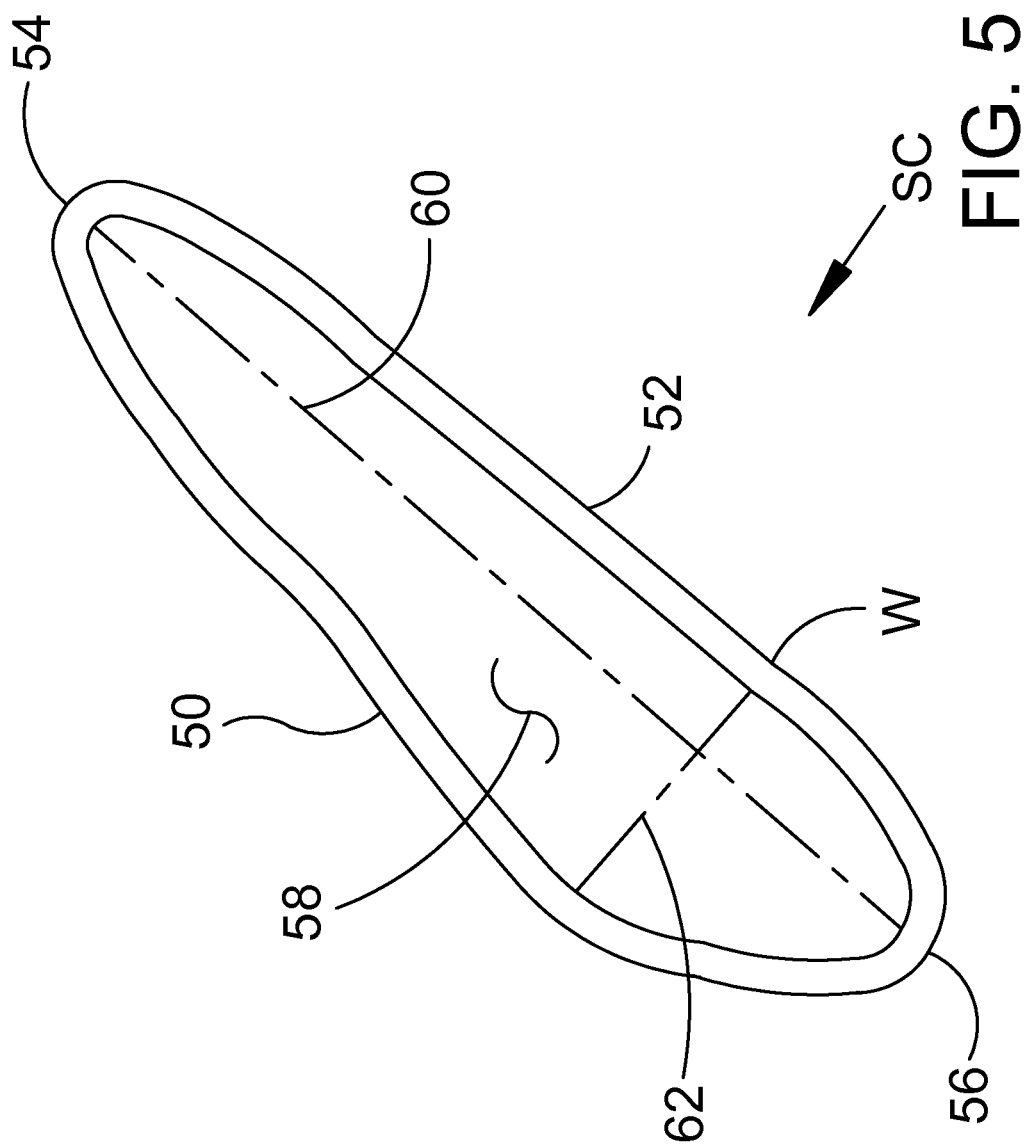
FIG. 5 is an enlarged cross-sectional view further illustrating Schlemm's canal SC shown in the previous figure.

FIG. 5 is an enlarged cross-sectional view further illustrating Schlemm's canal SC shown in the previous figure. With reference to FIG. 5, Schlemm's canal SC comprises a wall W defining a lumen 58. The shape of Schlemm's canal SC is somewhat irregular and can vary from patient to patient. The shape of Schlemm's canal SC may be conceptualized as a cylindrical-tube that has been partially flattened. The cross-sectional shape of lumen 58 may be compared to the shape of an ellipse. A major axis 60 and a minor axis 62 of lumen 58 are illustrated with dashed lines in FIG. 5.

The length of major axis 60 and minor axis 62 can vary from patient to patient. The length of minor axis 62 is between one and thirty micrometers in most patients. The length of major axis 60 is between one hundred and fifty micrometers and three hundred and fifty micrometers in most patients.

With reference to FIG. 5, Schlemm's canal SC comprises a first major side 50, a second major side 52, a first minor side 54, and a second minor side 56. In the embodiment of FIG. 5, first major side 50 is longer than both first minor side 54 and second minor side 56. Also in the embodiment of FIG. 5, second major side 52 is longer than both first minor side 54 and second minor side 56.

FIG. 6A is a perspective view showing a delivery system 100 including an ocular implant 150 and a cannula 108 defining a passageway that is dimensioned to slidingly receive ocular implant 150. Delivery system 100 may be used to advance ocular implant 150 into a target location in the eye of a patient. Examples of target locations that may be suitable in some applications include areas in and around Schlemm's canal, the trabecular meshwork, the suprachoroidal space, and the anterior chamber of the eye. FIG. 6B is an enlarged detail view further illustrating ocular implant 150 and cannula 108 of delivery system 100.

Delivery system 100 of FIG. 6A is capable of controlling the advancement and retraction of ocular implant 150 within cannula 108. Ocular implant 150 may be placed in a target location (e.g., Schlemm's canal) by advancing the ocular implant through a distal opening 132 of cannula 108 while the distal opening is in fluid communication with Schlemm's canal. In the embodiment of FIG. 6A, ocular implant 150 has been advanced through distal opening 132 of cannula 108 for purposes of illustration.

Delivery system 100 of FIG. 6A includes a housing 102, a sleeve 104, and an end cap 110. A tracking wheel 106 extends through a wall of housing 102 in FIG. 6A. Tracking wheel 106 is part of a mechanism that is capable of advancing and retracting a delivery tool 152 of delivery system 100. The delivery tool 152 extends through a distal opening of cannula 108 of FIG. 6B. Rotating the tracking wheel will cause delivery tool 152 to move in an axial direction along a passageway defined by cannula 108. The axial direction may be in a distal direction D or a proximal direction P.

In the embodiment of FIG. 6A, housing 102 is configured to be gripped with one hand while providing control over the axial advancement and retraction of ocular implant via tracking wheel 106. The housing of delivery system 100 results in an advantageous ergonomic relationship of the fingers relative to the hand. This design provides a configuration that will allow a user, such as a physician, to stabilize the device using part of the hand, while leaving the middle or index finger free move independently from the remainder of the hand. The middle or index finger is free to move independently to rotate the wheel for advancing and/or retract the ocular implant.

Figure 6:
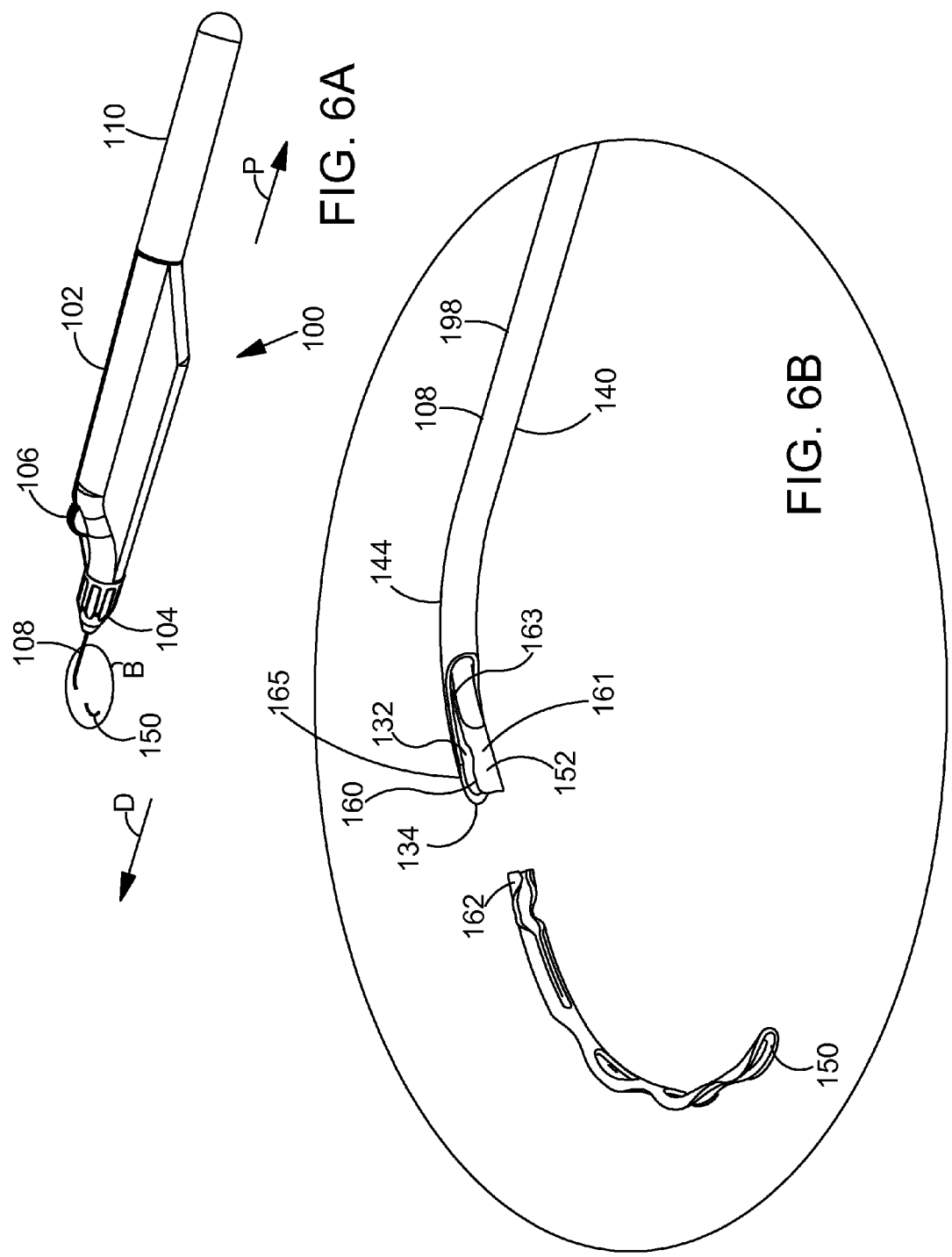
FIG. 6A is a perspective view showing a delivery system including an ocular implant and a cannula defining a passageway that is dimensioned to slidingly receive the ocular implant.
FIG. 6B is an enlarged detail view further illustrating the ocular implant and the cannula 108 shown in FIG. 6A.

FIG. 6B is an enlarged detail view further illustrating ocular implant 150 and a cannula 108 of delivery system 100. Cannula 108 comprises a generally tubular member 198 having proximal portion 140, a distal end 134, and a distal portion 144 extending between distal end 134 and proximal portion 140. In the embodiment of FIG. 6, distal portion 144 is curved. In some useful embodiments, distal portion 144 is dimensioned and configured to be received in the anterior chamber of the eye.

FIG. 6B shows delivery tool 152 of delivery system 100 extending through distal opening 132 of cannula 108. Delivery tool 152 includes an interlocking portion 160 that is configured to form a connection with a complementary interlocking portion 162 of ocular implant 150, as explained in more detail below. In the embodiment of FIG. 6, rotating the tracking wheel will cause delivery tool 152 and ocular implant 150 to move along a path defined by cannula 108. Cannula 108 is sized and configured so that the distal end of cannula 108 can be advanced through the trabecular meshwork of the eye and into Schlemm's canal. Positioning cannula 108 in this way places distal opening 132 in fluid communication with Schlemm's canal. Ocular implant 150 may be placed in Schlemm's canal by advancing the ocular implant through distal opening 132 of cannula 108 while the distal opening is in fluid communication with Schlemm's canal. The distal portion of the cannula may include a cutting portion configured to cut through the trabecular meshwork and the wall of Schlemm's canal, such as by providing distal end 134 with a sharp edge adapted to cut through such tissue.

Figure 7:
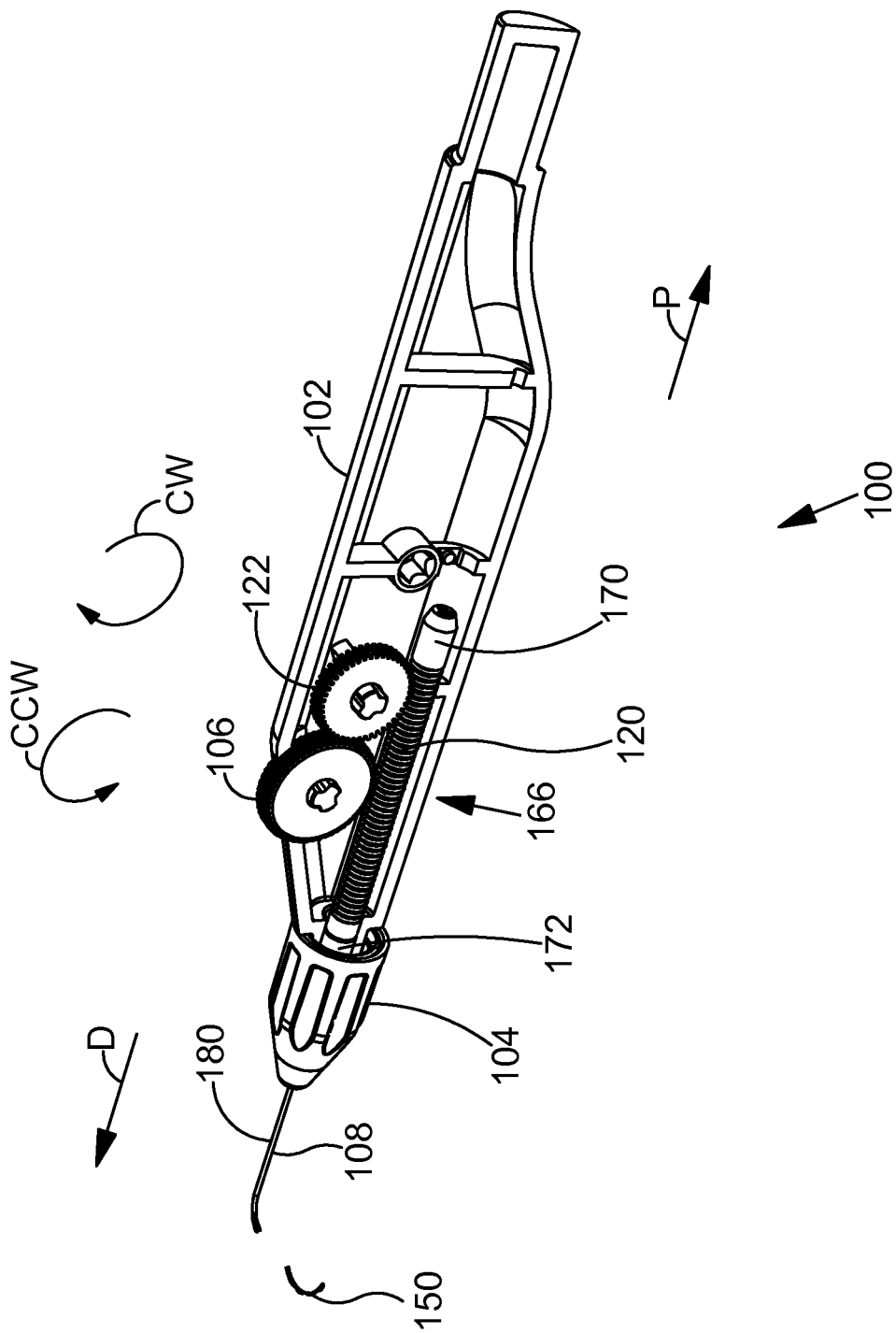
FIG. 7 is a perspective view further illustrating delivery system 100 shown in FIG. 6.

FIG. 7 is a perspective view further illustrating delivery system 100 shown in the previous figure. In FIG. 7, a portion of housing 102 has been removed for purposes of illustration. Delivery system 100 includes a delivery tool subassembly 170 and a cannula subassembly 180. Delivery tool subassembly 170 includes rotating rack gear 120 and a delivery tool (not shown). In the embodiment of FIG. 7, the delivery tool extends into a passageway defined by a cannula 108. Cannula 108 can be seen extending beyond sleeve 104 in FIG. 7. Cannula subassembly 180 includes cannula 108, a hub 172, and an extension tube (not shown). In the embodiment of FIG. 7, the extension tube of cannula subassembly 180 is disposed inside a lumen defined by rotating rack gear 120.

Delivery system 100 includes a mechanism 166 that controls the movement of delivery tool subassembly 170. Mechanism 166 includes a number of components that are located inside housing 102, including tracking wheel 106, an idler gear 122, and the rotating rack gear 120. In the embodiment of FIG. 7, tracking wheel 106 and idler gear 122 are both rotatably supported by housing 102. Gear teeth on tracking wheel 106 engage gear teeth on idler gear 122, which in turn engage gear teeth on the rotating rack gear 120. Rotating tracking wheel 106 in a counter clockwise direction CCW causes idler gear 122 to rotate in a clockwise direction CW, which in turn causes the rotating rack gear 120 to move in a distal direction D. Rotating tracking wheel 106 in a clockwise direction CW causes idler gear 122 to rotate in a counter clockwise direction CCW, which in turn causes the rotating rack gear 120 to move in a proximal direction P. In other embodiments, the idler gear may be eliminated from the device, which would cause counter-clockwise movement of the tracking wheel to move the rack gear proximally.

In the embodiment of FIG. 7, a sleeve 104 is fixed to cannula subassembly 180. Sleeve 104 may be rotated by the user to change the orientation of cannula 108 with respect to housing 102. The sleeve 104 may include gripping features, such as grooves (as shown), a rubber coating, or other frictional surfaces to facilitate this use. In some applications, correct alignment between the cannula and iris is advantageous to ensure that the core tube and/or ocular implant is advanced at the correct trajectory relative to Schlemm's canal or other anatomy in the eye into which the ocular implant is to be implanted. The device is configured in a manner that keeps the ocular implant aligned within the device during rotation. Selected groups of components are keyed together to ensure that they rotate as a single body while simultaneously allowing axial movement of the ocular implant. In the embodiment of FIG. 7, cannula subassembly 180 and delivery tool subassembly 170 rotate in unison with sleeve 104 relative to housing 102.

In the embodiment of FIG. 7, rotating rack gear 120 is configured to rotate with sleeve 104 while maintaining the ability to move axially in the distal and proximal directions before, during, and after rotation. As the rotating rack gear 120 moves distally and/or proximally, it causes corresponding movement of the delivery tool relative to cannula 108. This movement is transferred to ocular implant 150 when delivery tool 152 is coupled to ocular implant 150. Delivery tool subassembly 170 and cannula subassembly 180 engage one another in a keyed arrangement, as described in more detail below. This keyed arrangement causes delivery tool subassembly 170 and cannula subassembly 180 to maintain a constant rotational orientation relative to each other while, at the same time, allowing delivery tool subassembly 170 to translate in a distal direction D and a proximal direction P relative to cannula subassembly 180.

Figure 8:
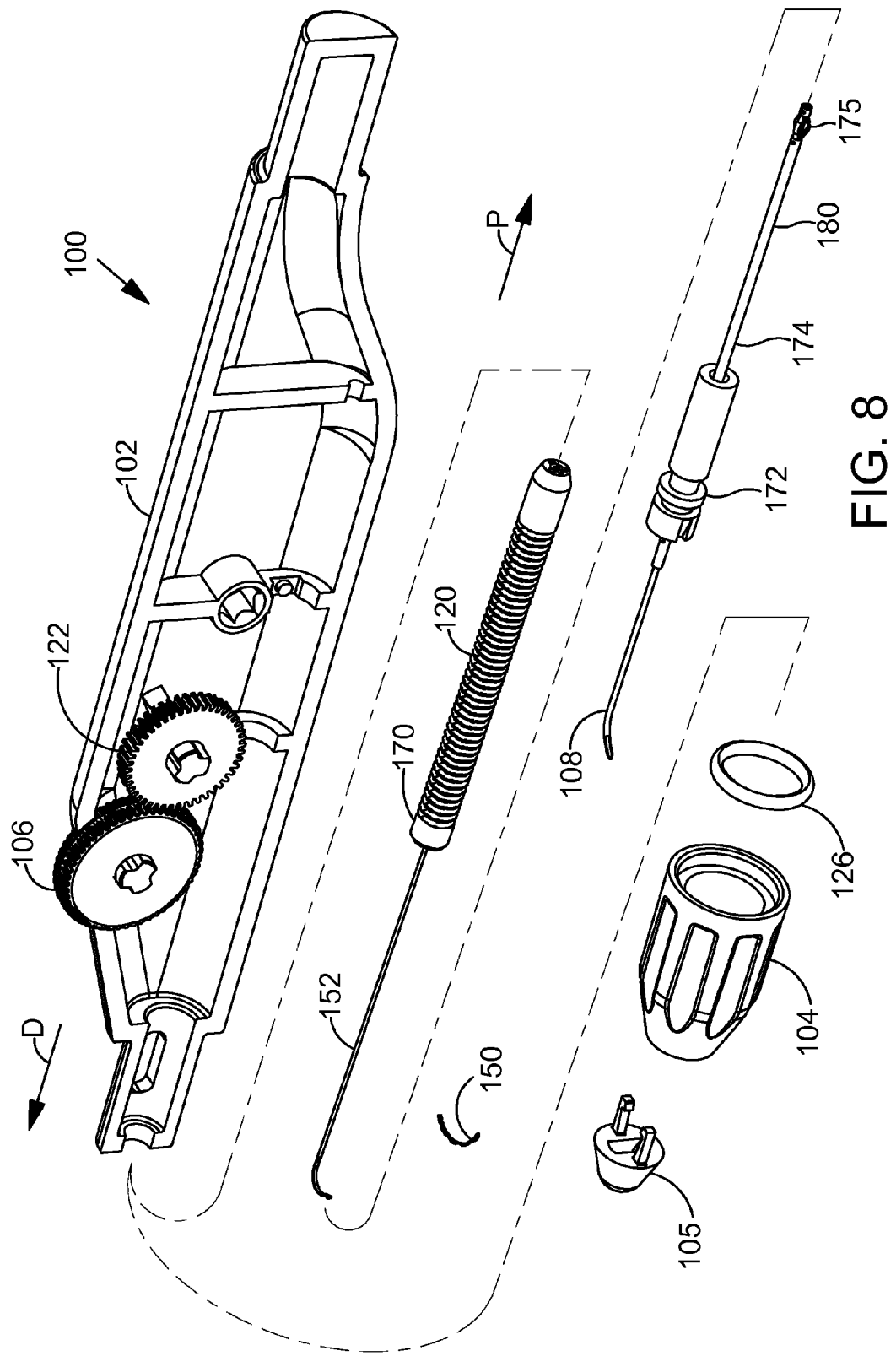
FIG. 8 is an exploded view illustrating various elements of a delivery system in accordance with the detailed description.

FIG. 8 is an exploded view illustrating various elements of delivery system 100. Cannula subassembly 180 includes a hub 172 and an extension tube 174 that are both fixed to cannula 108. Extension tube 174 includes a shaped portion 175 that is dimensioned and shaped to fit within a shaped through hole 177 (shown in FIGS. 8A and 11) within by rotating rack gear 120. This keyed arrangement causes delivery tool subassembly 170 and cannula subassembly 180 to maintain a constant rotational orientation relative to each other while, at the same time, allowing delivery tool subassembly 170 to translate in a distal direction D and a proximal direction P relative to cannula subassembly 180.

In some embodiments, delivery tool 152 is formed from shape memory material (such as, e.g., nitinol), and at least a portion of delivery tool 152 assumes a curved at-rest shape when no external forces are acting on it. Delivery tool 152 can be urged to assume a straightened shape, for example, by inserting delivery tool 152 through a straight portion of the passageway defined by cannula 108. When the delivery tool is confined, such as within cannula 108, the interlocking portion can engage the complementary interlocking portion to join the delivery tool and ocular implant together, and allow the delivery tool and ocular implant to move together through the cannula 108, as described in more detail below.

Delivery system 100 also includes an O-ring 126 disposed between sleeve and 104 and housing 102. O-ring 126 can provide friction and/or resistance between sleeve 104 and housing 102. This friction and/or resistance may be useful, for example, to hold the sleeve 104 in a desired orientation. A noseplug 105 snaps into the distal end of the delivery system.

Figure 11:
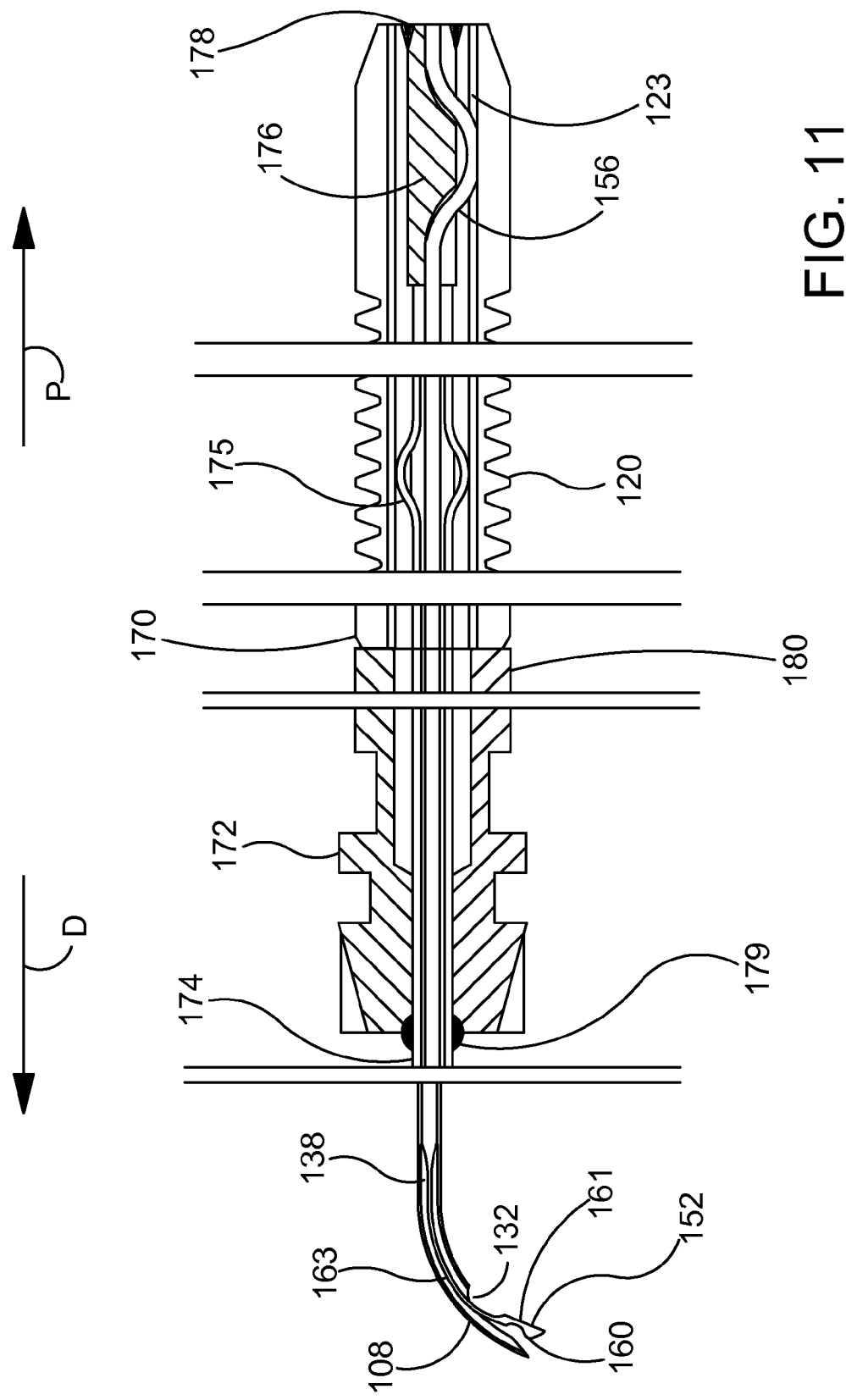
FIG. 11 is a cross-sectional view showing an assembly including both the delivery tool subassembly and the cannula subassembly shown in the exploded perspective view of FIG. 8.

FIG. 9 is an exploded perspective view of delivery tool subassembly 170 shown in the previous figure. Delivery tool subassembly 170 comprises a delivery tool 152, a rotating rack gear 120, and a spacer 176. Delivery tool 152 includes a shaped proximal portion 156, a curved distal portion 153, a distal cannula engagement surface 161 and a reduced diameter portion 163 proximal to the distal cannula engagement surface 161. Spacer 176 is interposed between rotating rack gear 120 and shaped proximal portion 156 of delivery tool 152 to hold delivery tool 152 and rotating rack gear 120 in a generally co-axial arrangement when delivery tool subassembly 170 is in an assembled state, as shown in FIG. 11. Distal cannula engagement surface 161 is adapted to slide along an inside surface of the cannula wall while the delivery tool 152 is engaged to ocular implant 150. Curved distal portion 153 of delivery tool 152 has an at rest curve that is greater (i.e., has a smaller radius of curvature) than the curved portion 144 of cannula 108.

FIG. 10 is an exploded perspective view of cannula subassembly 180. Cannula subassembly 180 comprises cannula 108, extension tube 174 and hub 172. In the embodiment of FIG. 10, cannula 108 defines a passageway 138 that is dimensioned to slidingly receive an ocular implant and the delivery tool shown in the previous figure. At the same time, extension tube 174 of cannula subassembly 180 may be received inside a lumen defined by the rotating rack gear shown in the previous figure.

Extension tube 174 includes a shaped portion 175 that is dimensioned and shaped to fit within a shaped through hole defined by rotating rack gear 120, as shown below in FIG. 11. This keyed arrangement causes delivery tool subassembly 170 and cannula subassembly 180 to maintain a constant rotational orientation relative to each other while, at the same time, allowing delivery tool subassembly 170 to translate in a distal direction D and a proximal direction P relative to cannula subassembly 180.

Figure 8A:
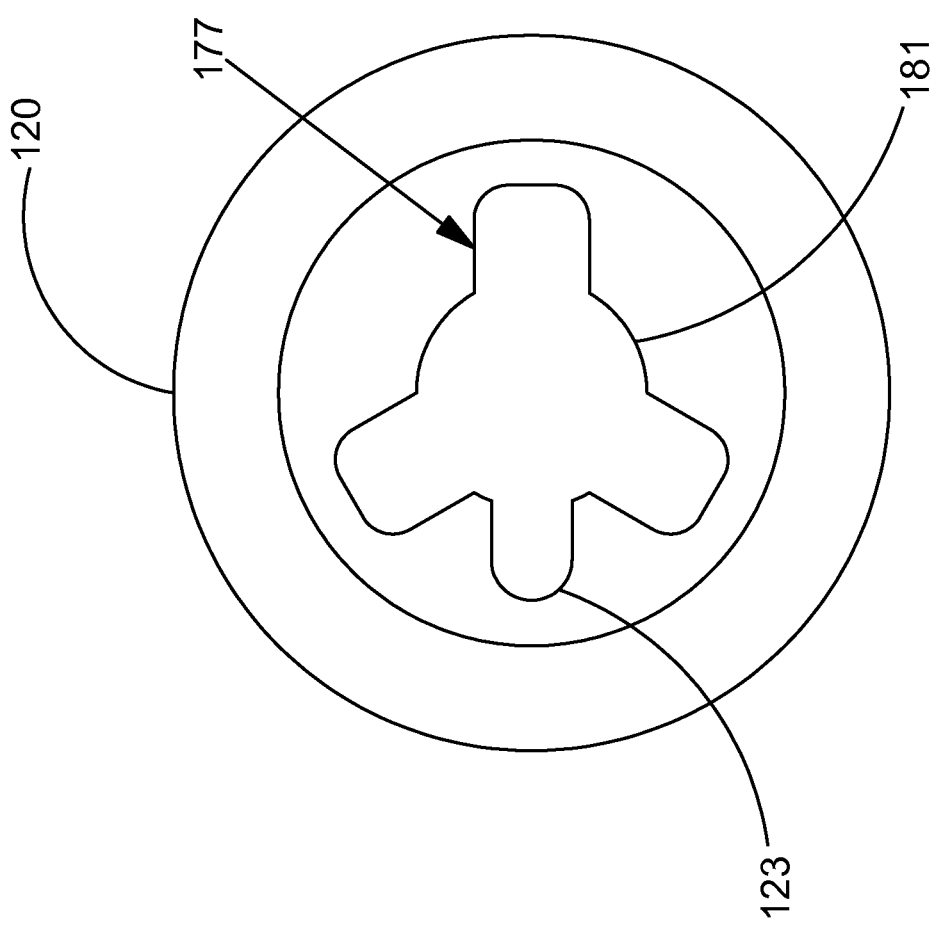
FIG. 8A is an end view of the rotating rack gear shown in FIG. 8.

FIG. 11 is a cross-sectional view showing an assembly including delivery tool subassembly 170 and cannula subassembly 180 discussed above. Delivery tool subassembly 170 includes a delivery tool 152, a rotating rack gear 120 and a spacer 176. In the cross-sectional view of FIG. 11, a shaped portion 156 of delivery tool 152 can be seen extending into a slot 123 extending from a central portion 181 a through hole 177 formed in rotating rack gear 120. (FIG. 8A shows an end view of rotating rack gear 120 and through hole 177.) In the embodiment of FIG. 11, an interlocking portion 160 of delivery tool 152 is disposed in angular alignment with shaped portion 156. Spacer 176 is interposed between rotating rack gear 120 and delivery tool 152. In the exemplary embodiment of FIG. 11, spacer 176 is shaped and dimensioned to hold delivery tool 152 and rotating rack gear in a generally co-axial arrangement. This arrangement creates an advantageous oriented relationship of interlocking portion 160 with respect to the distal opening 132 of cannula 108 and ensures that interlocking portion 160 is unimpeded and readily disengages itself from the implant when it exits and flexes through distal opening 132. In the exemplary embodiment of FIG. 11, spacer 176 and rotating rack gear 120 are fixed to each other at a weld joint 178. Weld joint 178 may be formed, for example, using a laser welding process.

Cannula subassembly 180 includes cannula 108, a hub 172, and an extension tube 174. Extension tube 174 is disposed about cannula 108. Extension tube 174 and cannula 108 may be fixed to one another, for example, using a laser spot welding process. Hub 172 is fixed to an outer surface portion of extension tube 174 in the embodiment of FIG. 11. In FIG. 11, extension tube 174 of cannula subassembly 180 can be seen extending into a shaped through-hole defined by rotating rack gear 120 of delivery tool assembly 170.

In FIG. 11, delivery tool 152 can be seen extending into a passageway 138 defined by a cannula 108 of cannula subassembly 180. Passageway 138 defined by cannula 108 is sized to slidably enclose delivery tool 152 and an ocular implant that is coupled to delivery tool 152. Delivery tool 152 is configured to form a connection with the ocular implant, so that distal movement of the delivery tool can cause distal movement of the ocular implant within cannula 108. Delivery tool 152 may be used to advance the ocular implant through a distal opening 132 of cannula 108 in order to deliver the ocular implant into the eye. The assembly of FIG. 11 may be rotated by the user to change the orientation of the curved portion of cannula 108 with respect to the housing of the delivery system. The keyed relationship between delivery tool subassembly 170 and cannula subassembly 180 assures that the rotational orientation between cannula 108 and the ocular implant/delivery tool stays constant while at the same time, allowing ocular implant/delivery tool to translate in a distal direction D and a proximal direction P relative to cannula 108.

Figure 12:
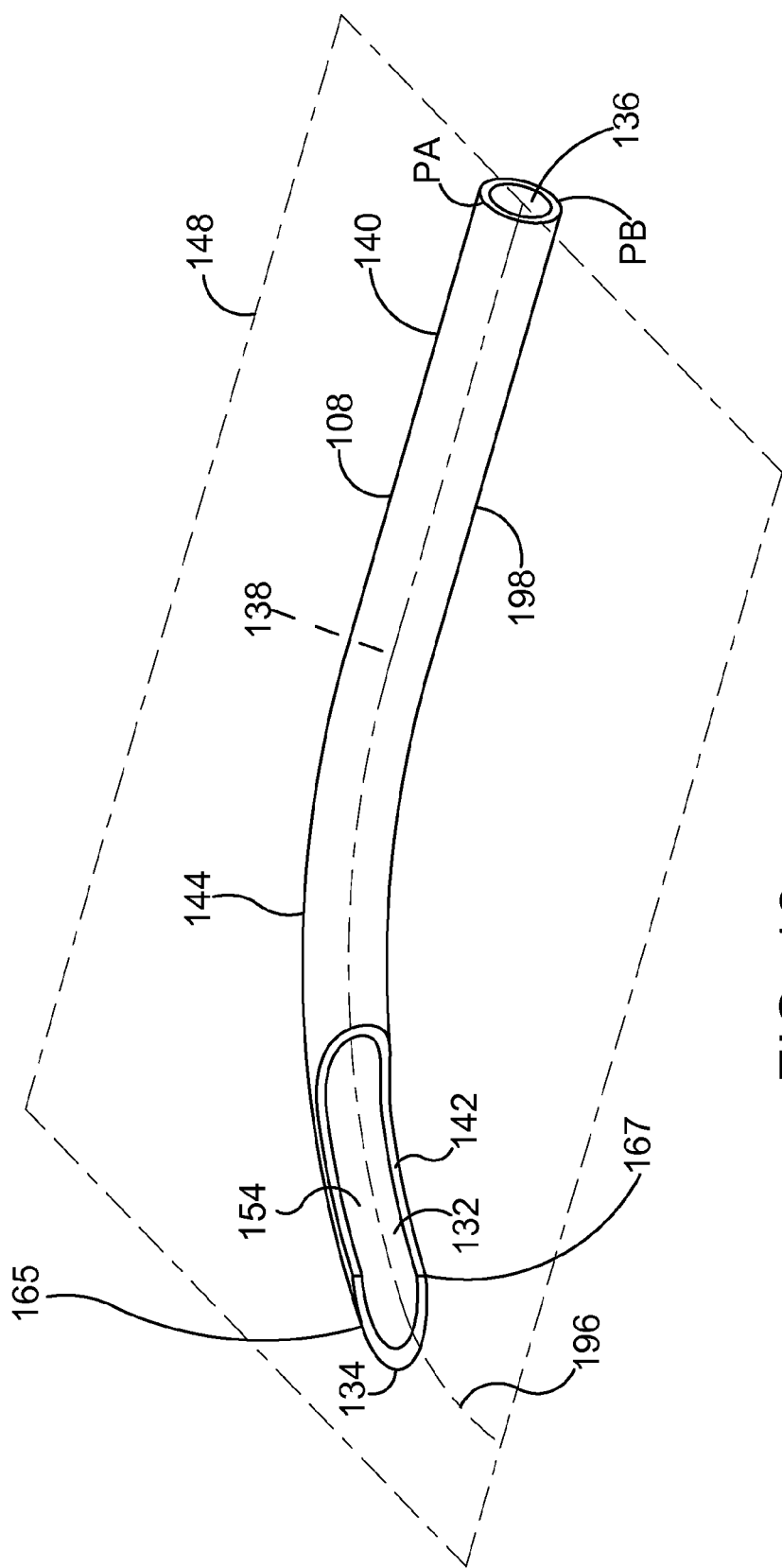
FIG. 12 is a perspective view of a cannula in accordance with the detailed description.

FIG. 12 is a perspective view of a cannula 108 in accordance with the present detailed description. Cannula 108 of FIG. 12 comprises a generally tubular member 198 having a central axis 196. Generally tubular member 198 of FIG. 12 comprises a proximal portion 140, a distal end 134, and a distal portion 144 extending between distal end 134 and proximal portion 140. A distal opening surface 142 surrounds a distal opening 132 extending through the distal end and through a side wall of cannula 108. A beveled edge 165 is disposed at the distal end of distal opening surface 142, extending from the distal end 134 to a proximal extent 167 of beveled edge 165. Tubular member 198 defines distal opening 132, a proximal opening 136, and a passageway 138 extending between proximal opening 136 and distal opening 132.

In the embodiment of FIG. 12, proximal portion 140 of cannula 108 is substantially straight, distal portion 144 of cannula 108 is curved, and central axis 196 defines a curvature plane 148. Curvature plane 148 may be referred to as a plane of curvature. Curvature plane 148 divides cannula 108 into a first portion PA and a second portion PB. In the embodiment of FIG. 12, second portion PB is substantially a mirror image of first portion PA. In FIG. 12, distal portion 144 is shown extending between distal end 134 and proximal portion 140 with no intervening elements. In the embodiment of FIG. 12, distal portion 144 is curved along its entire length.

A method in accordance with this detailed description may include the step of advancing the distal end 134 of cannula 108 through the cornea of a human eye so that distal end 134 is disposed in the anterior chamber of the eye. Cannula 108 may then be used to access Schlemm's canal of the eye, for example, by piercing the wall of Schlemm's canal with the distal end 134 of cannula 108. The beveled edge 165 may be inserted into Schlemm's canal to place at least part of distal opening 132 of cannula 108 in communication with Schlemm's canal, as discussed in more detail below. The ocular implant may be advanced out of a distal port of the cannula and into Schlemm's canal.

In the embodiment of FIG. 12, distal portion 144 of cannula 108 defines a trough 154. In some useful embodiments, trough 154 is configured to receive the entire external cross section of an ocular implant as the ocular implant is being advanced into Schlemm's canal. When this is the case, trough 154 may have a depth dimension that is deeper than a width of the ocular implant. This cannula configuration advantageously prevents the ocular implant from intersecting the layers of the trabecular meshwork as the ocular implant is advanced into Schlemm's canal. Trough 154 may also be configured to allow the proximal portion of the ocular implant to be released from the delivery tool, as discussed below.

Figure 13:
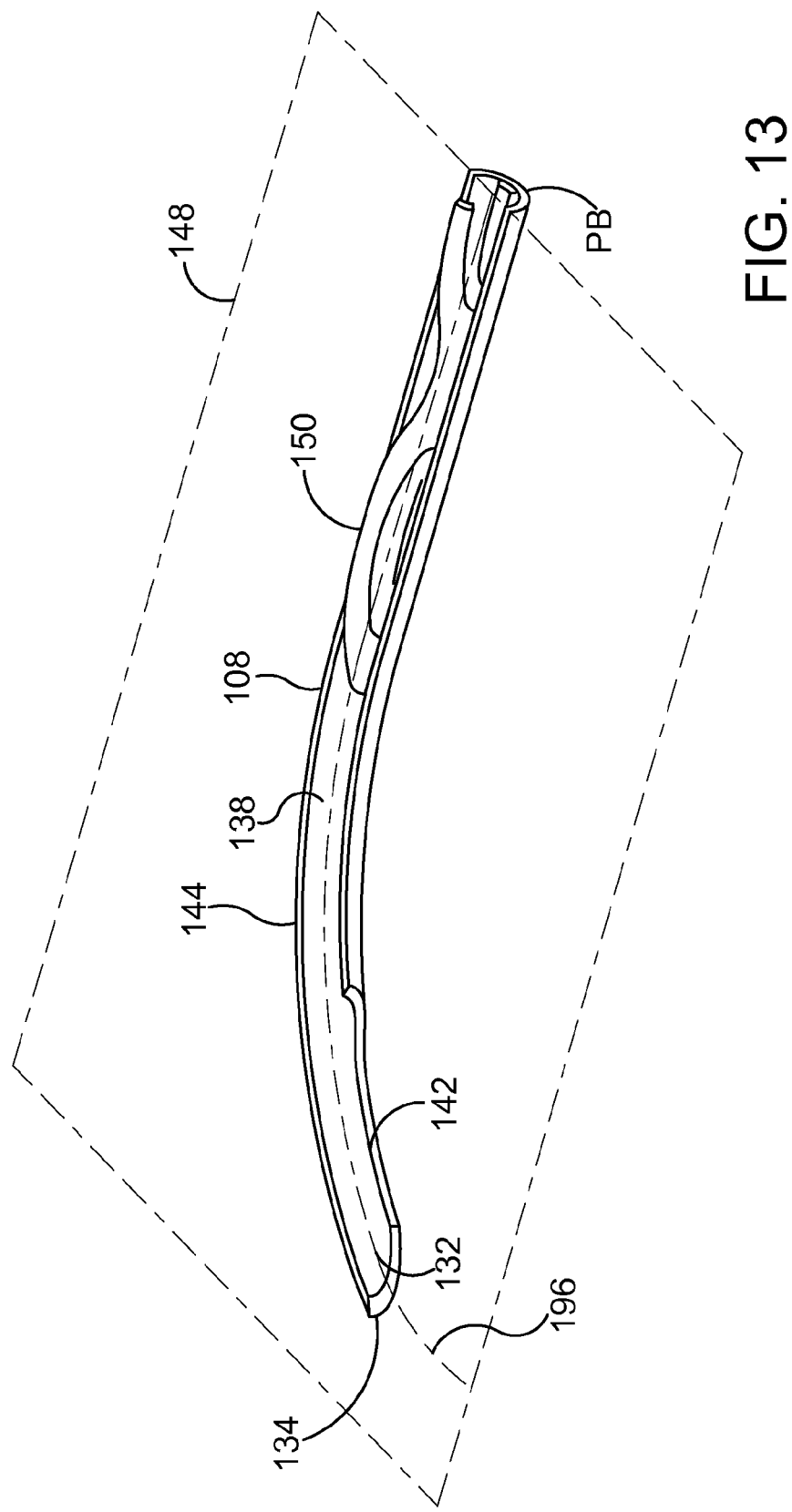
FIG. 13 is a perspective view of an assembly including the cannula shown in FIG. 12 and an ocular implant that is resting in a passageway defined by the cannula.

FIG. 13 is a perspective view of an assembly including cannula 108 shown in the previous figure. For purposes of illustration, cannula 108 is cross-sectionally illustrated in FIG. 13. In FIG. 13, an ocular implant 150 can be seen resting in a passageway 138 defined by cannula 108. With reference to FIG. 13, it will be appreciated that distal portion 144 of cannula 108 is curved so that central axis 196 of cannula 108 defines a curvature plane 148. With reference to FIG. 13, it will be appreciated that curvature plane 148 divides cannula 108 into a first portion and a second portion PB. Only second portion PB of cannula 108 is shown in the illustrative embodiment of FIG. 13.

Figure 14:
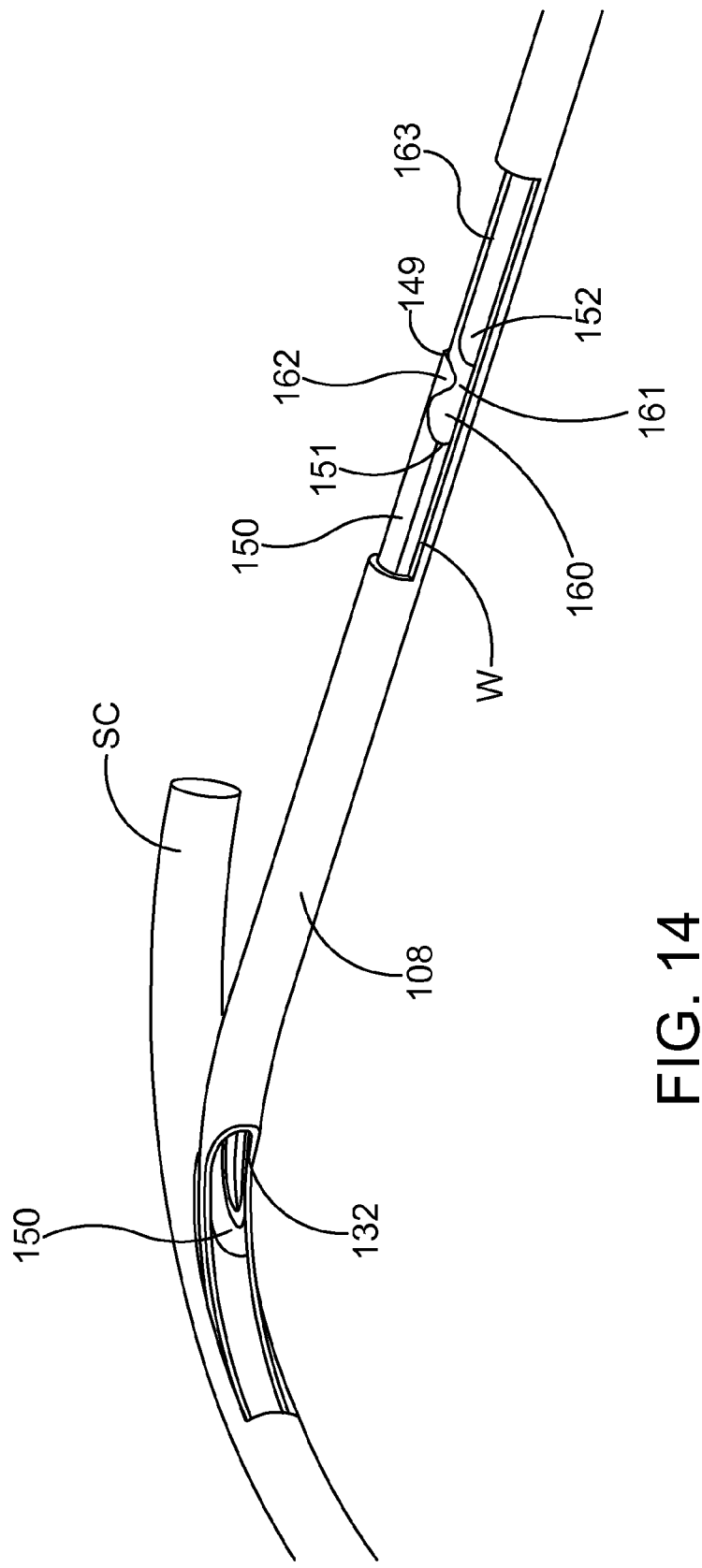
FIG. 14 is a stylized perspective view including the assembly shown in FIG. 13.

FIG. 14 is a stylized perspective view including the assembly shown in the previous figure. In the embodiment of FIG. 14, a distal portion of cannula 108 is shown extending through the wall of Schlemm's canal SC. The distal tip of cannula 108 may include a sharp portion configured for cutting and/or pierced the trabecular meshwork and the wall of Schlemm's canal so that the passageway defined by the cannula can be placed in fluid communication with the lumen defined by Schlemm's canal. With the passageway of the cannula placed in fluid communication with the lumen of Schlemm's canal, ocular implant 150 can be advanced out of the distal opening of the cannula and into Schlemm's canal. In FIG. 14, a distal portion of ocular implant 150 can be seen through distal opening 132 of cannula 108.

For purposes of illustration, a hypothetical window W is cut through the wall of cannula 108 in FIG. 14. An interlocking portion 160 of a delivery tool 152 and a complementary interlocking portion 162 of ocular implant 150 are visible through window W. In the embodiment of FIG. 14, interlocking portion 160 of delivery tool 152 and complementary interlocking portion 162 of ocular implant 150 are engaging each other so that a proximal end 149 of ocular implant 150 is proximal to the distal end 151 of delivery tool 152. Surface 161 of delivery tool 152 rests against the wall of cannula 108 to prevent interlocking portion 160 of delivery tool 152 and complementary interlocking portion 162 of ocular implant 150 from disengaging one another. When they are connected in this fashion, delivery tool 152 and ocular implant 150 move together as the delivery tool is advanced and retracted relative to cannula 108 by the delivery system mechanism.

Figure 15:
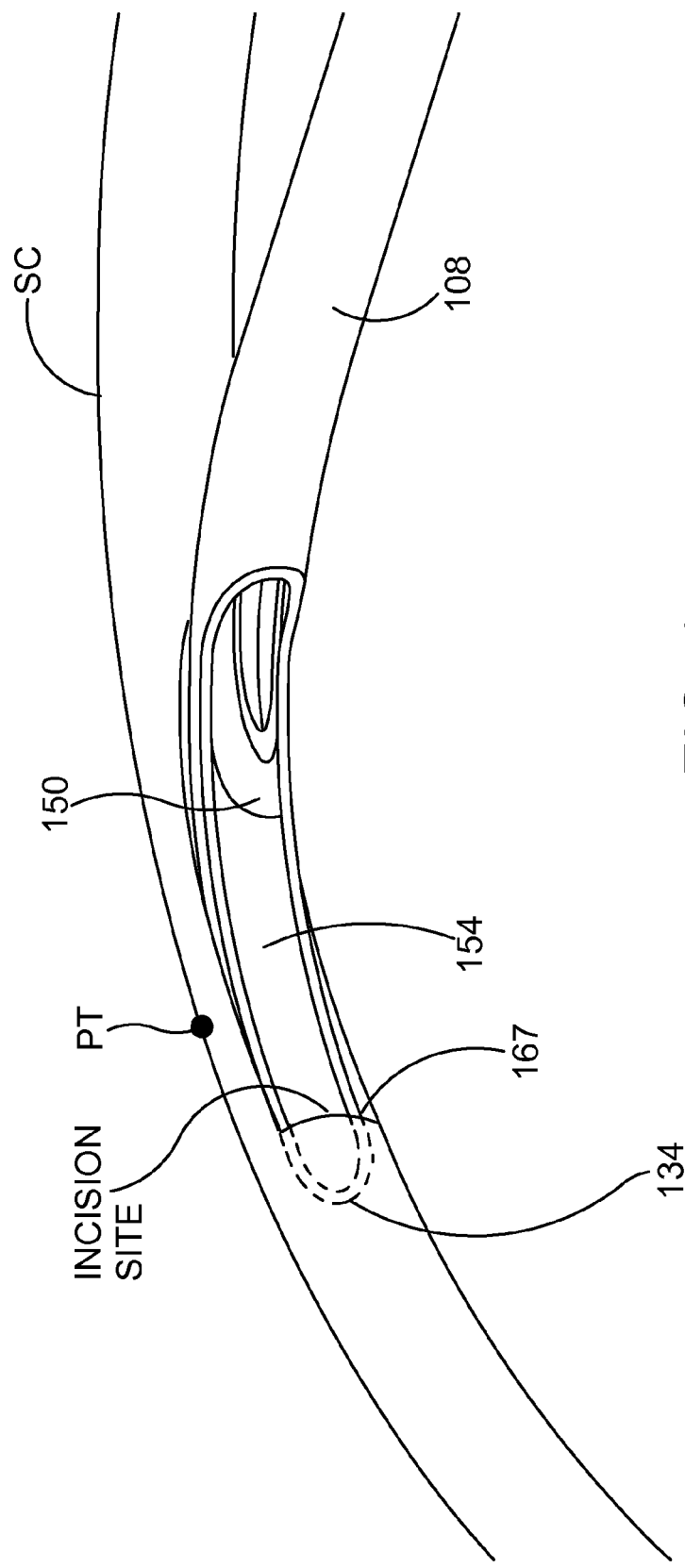
FIG. 15 is an enlarged perspective view showing a portion of the cannula shown in the assembly of FIG. 14.

FIG. 15 is an enlarged perspective view showing a portion of cannula 108 shown in the previous figure. In some useful embodiments, cannula 108 is curved to achieve substantially tangential entry into Schlemm's canal SC. In the embodiment of FIG. 15, cannula 108 is contacting an outer major wall of Schlemm's canal SC at a point of tangency PT. Also in the embodiment of FIG. 15, a curved distal portion of cannula 108 is dimensioned to be disposed within the anterior chamber of the eye.

As shown in FIG. 15, the distal tip 134 and beveled edge of the cannula 108 have been inserted into Schlemm's canal up to the proximal extent 167 of beveled edge 165. In this position, ocular implant 150 can be seen extending into trough 154. In some useful embodiments, the ocular implant has a radius of curvature that is larger than the radius of curvature of the cannula. This arrangement ensures that the ocular implant will track along trough 154 as the ocular implant is urged in a distal direction by delivery system 100.

Figure 16:
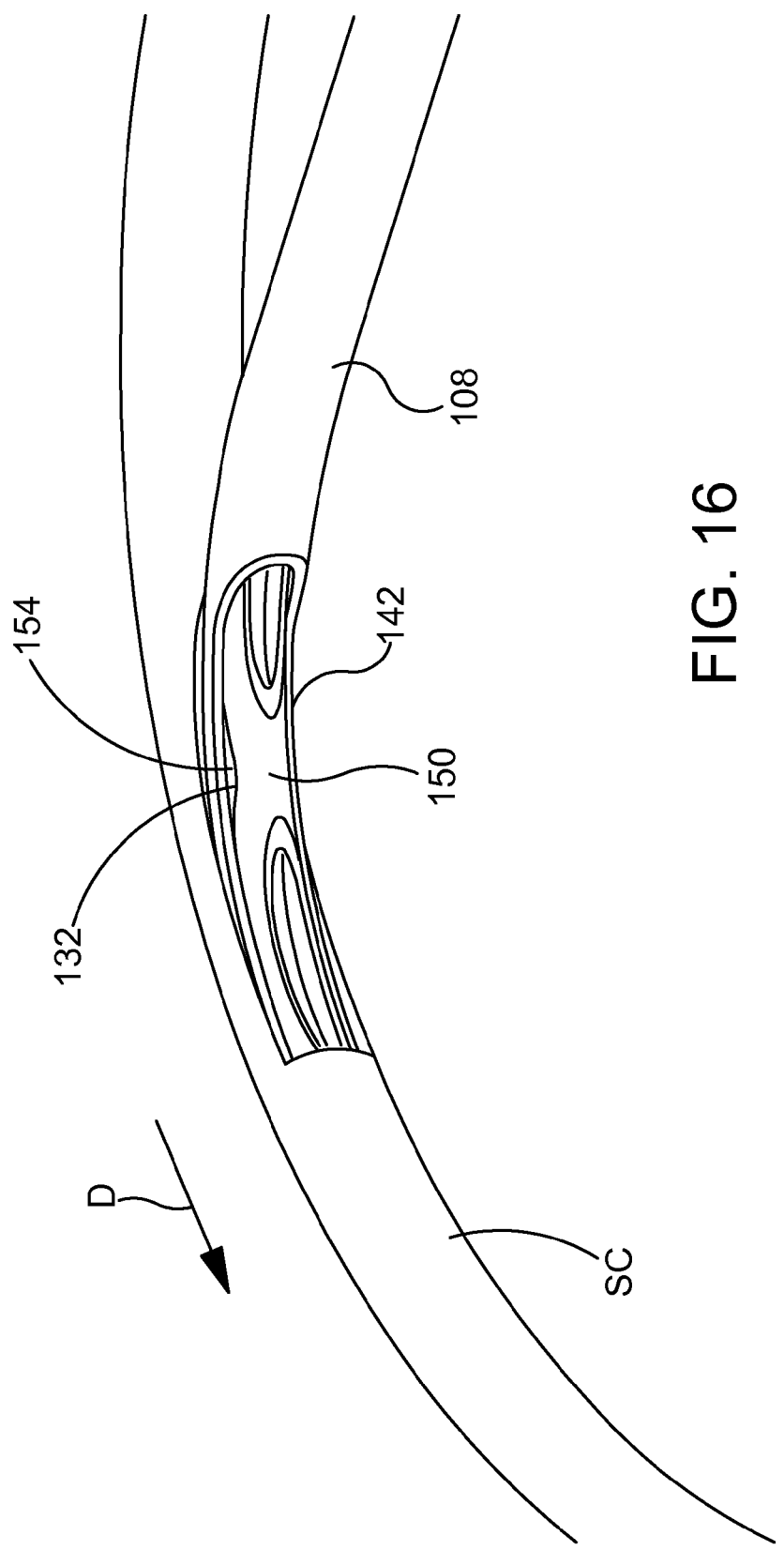
FIG. 16 is an additional perspective view showing the ocular implant and the cannula shown in the previous Figure.

FIG. 16 is an additional perspective view showing ocular implant 150 and cannula 108 shown in the previous figure. By comparing FIG. 16 with the previous figure, it will be appreciated that ocular implant 150 has been advanced in a distal direction D while cannula 108 has remained stationary so that a distal portion of ocular implant 150 is disposed inside Schlemm's canal SC. Trough 154 opens into an elongate opening 132 defined by edge 142 at the distal portion of cannula 108. In the embodiment of FIG. 16, the elongate opening defined by the cannula provides direct visualization of the ocular implant as it is advanced into Schlemm's canal. A configuration allowing direct visualization of the ocular implant has a number of clinical advantages. During a medical procedure, it is often difficult to monitor the progress of the implant by viewing the implant through the trabecular meshwork. For example, blood reflux may push blood into Schlemm's canal obstructing a physician's view the portion of the implant that has entered Schlemm's canal. With reference to FIG. 16, ocular implant 150 tracks along trough 154 as it is advanced distally along cannula 108. The trough opening allows the physician to monitor the progress of the implant by viewing the implant structures as they advance through the trough prior to entering Schlemm's canal. The trough opening also allows the physician to identify the position of the proximal end of the ocular implant with respect to the incision made by the cannula to access Schlemm's canal.

Figure 17:
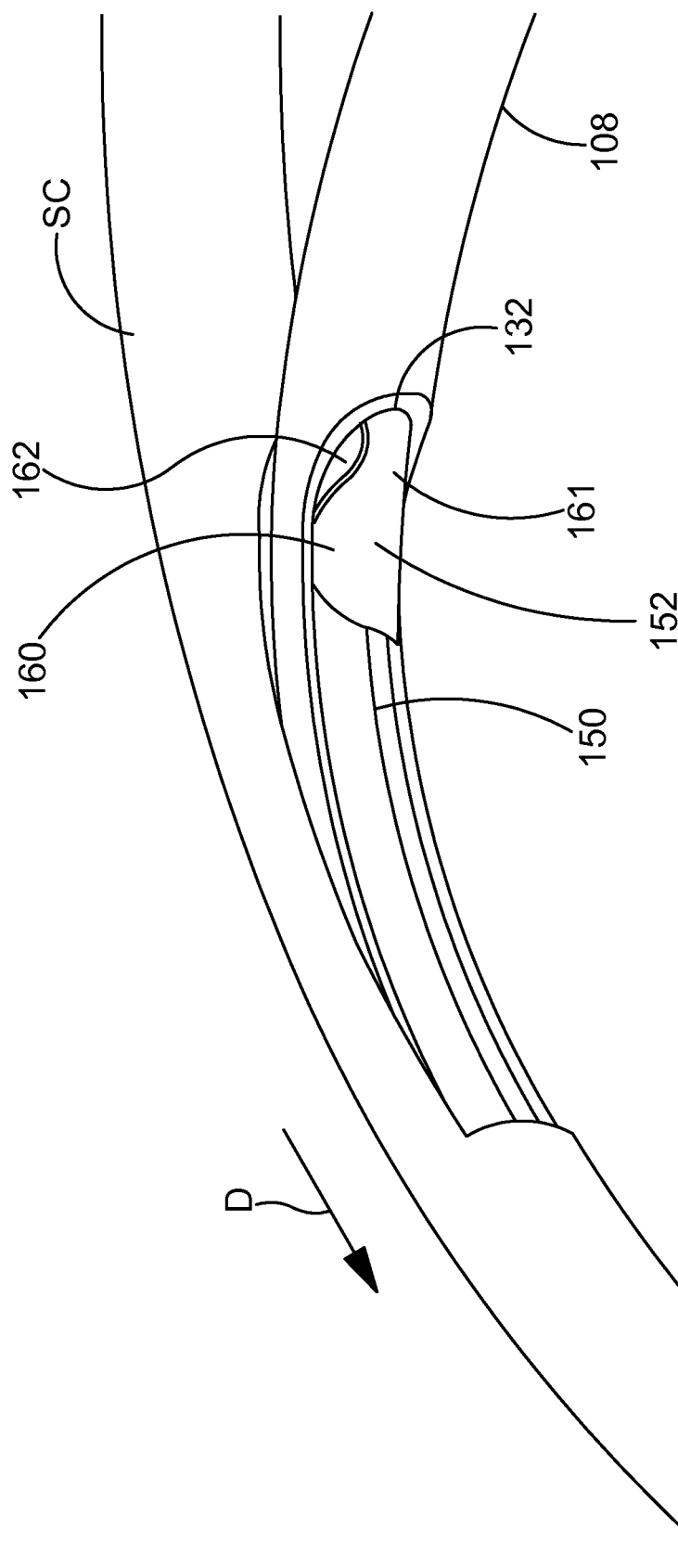
FIG. 17 is an additional perspective view showing the ocular implant and the cannula shown in FIG. 16.

FIG. 17 is an additional stylized perspective view showing ocular implant 150 and cannula 108. In the embodiment of FIG. 17, the interlocking portions 160 and 162 of the delivery tool 152 and ocular implant 150, respectively, can be seen entering the distal opening 132 defined by cannula 108. As shown, ocular implant 150 has been advanced in a distal direction D (relative to the embodiment shown in the previous figure) so that more of ocular implant 150 is disposed inside Schlemm's canal SC. Surface 161 opposite interlocking portion 160 of delivery tool 152 still rests against the inner wall of cannula 108 to keep the delivery tool interlocked with ocular implant 150.

Figure 18:
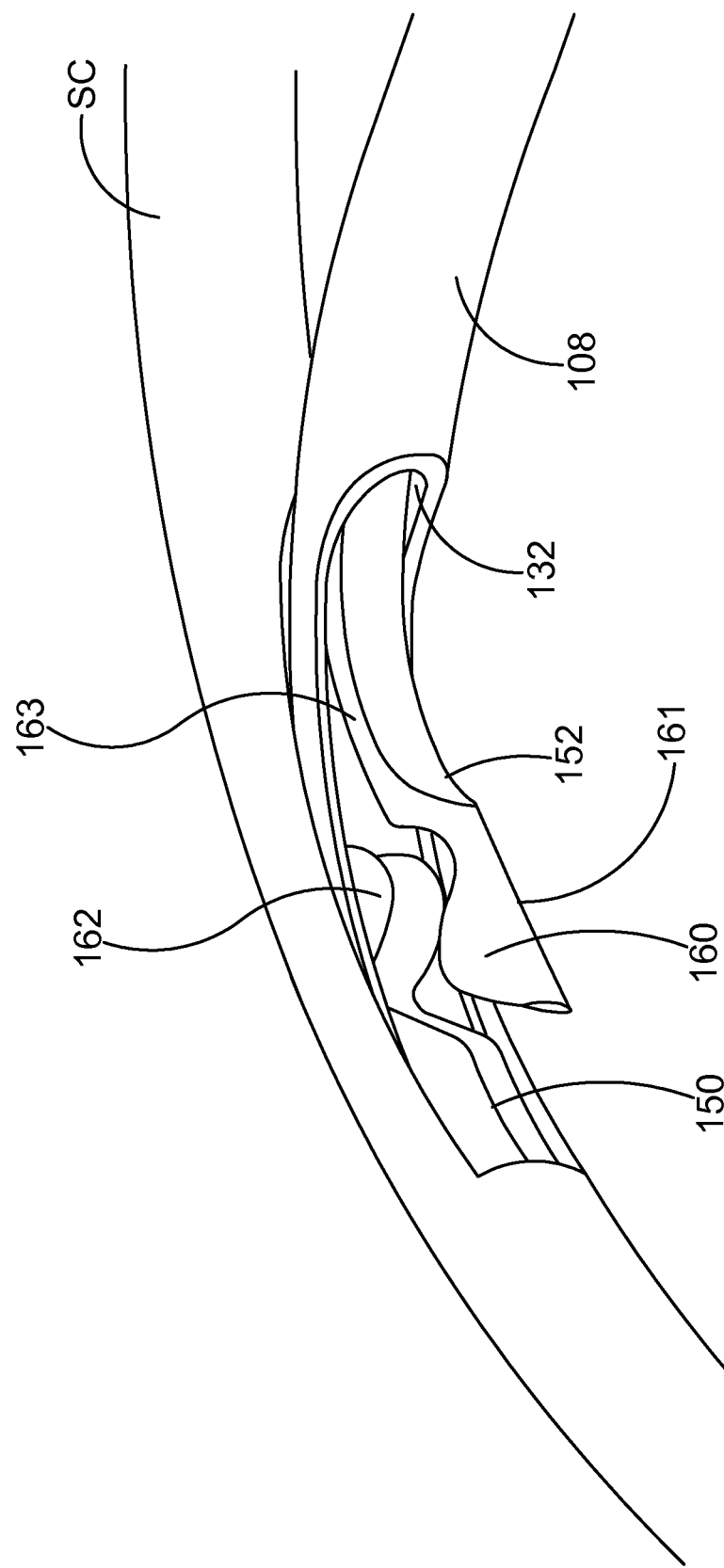
FIG. 18 is an additional perspective view showing the ocular implant and the cannula shown in FIGS. 16 and 17.

FIG. 18 is an additional stylized perspective view showing ocular implant 150 and cannula 108. As shown in FIG. 18, the ocular implant 150 and delivery tool 152 have advanced further distally so that delivery tool surface 161 and part of the reduced diameter portion 163 have now passed into opening 132, thereby permitting the delivery tool curved portion 153 to move toward its curved at-rest shape so that the delivery tool engagement surface 160 disengages and moves away from its complementary engagement surface 162 on the ocular implant 150.

In some useful embodiments, the delivery tool may be colored to provide visual differentiation from the implant. After the disengaging from the ocular implant, cannula 108 and delivery tool 152 can be withdrawn from Schlemm's canal SC leaving the ocular implant 150 in the fully deployed position shown in FIG. 18. After delivery of ocular implant 150 is complete, the delivery tool and the cannula may be removed from the eye, leaving at least a distal portion of the ocular implant in Schlemm's canal.

Figure 19:
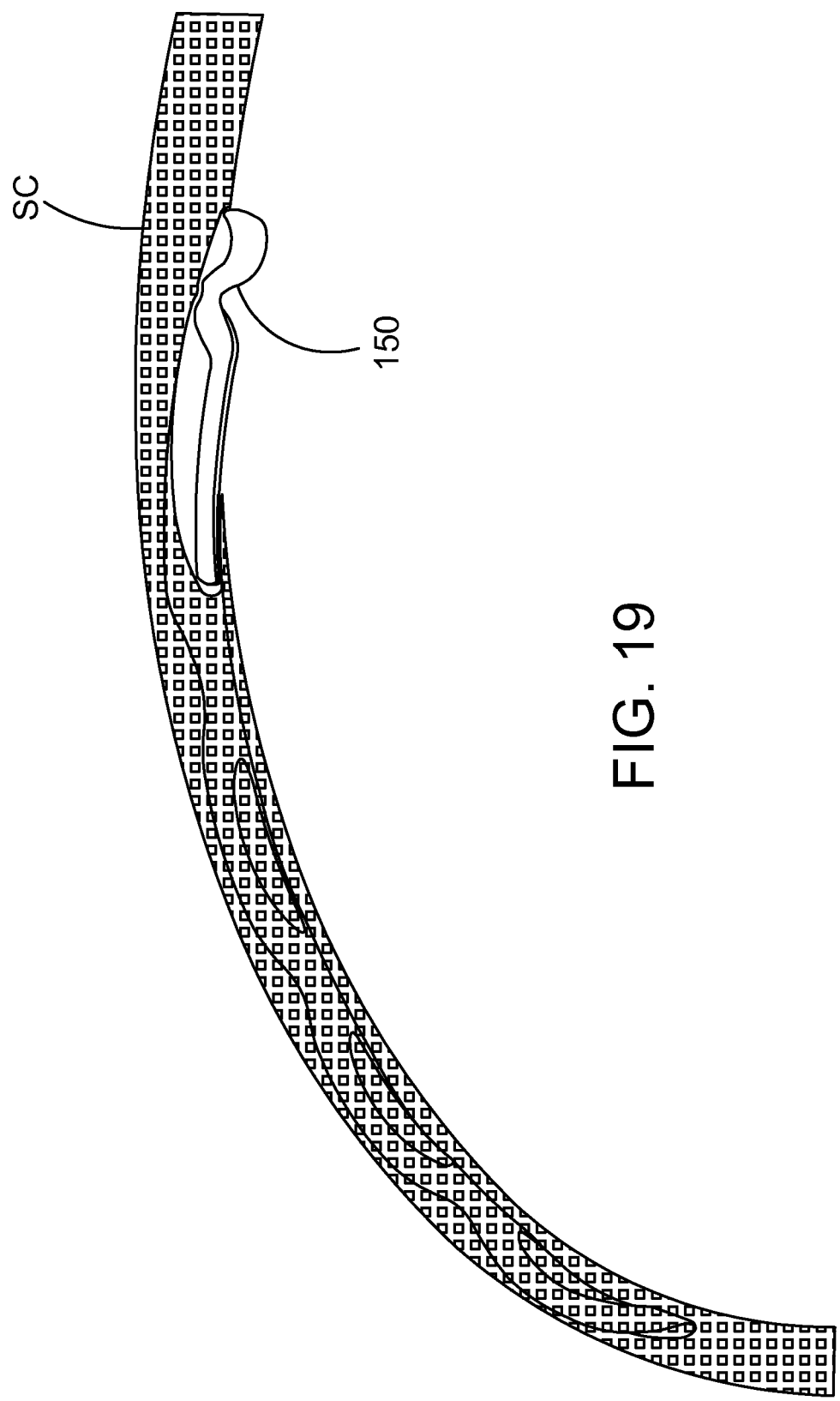
FIG. 19 is a perspective view of Schlemm's canal after the cannula shown in FIG. 18 has been withdrawn leaving an inlet portion of the ocular implant in the anterior chamber of the eye and the remainder of ocular implant in Schlemm's canal.

FIG. 19 is a perspective view of Schlemm's canal SC after the cannula (seen in the previous figure) has been withdrawn leaving an inlet portion of ocular implant 150 in the anterior chamber of the eye and the remainder of ocular implant 150 in Schlemm's canal. The presence of ocular implant 150 in Schlemm's canal may facilitate the flow of aqueous humor out of the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 150 will support the trabecular meshwork and Schlemm's canal tissue and will provide for improved communication between the anterior chamber and Schlemm's canal (via the trabecular meshwork) and between pockets or compartments along Schlemm's canal.

Figure 20A:
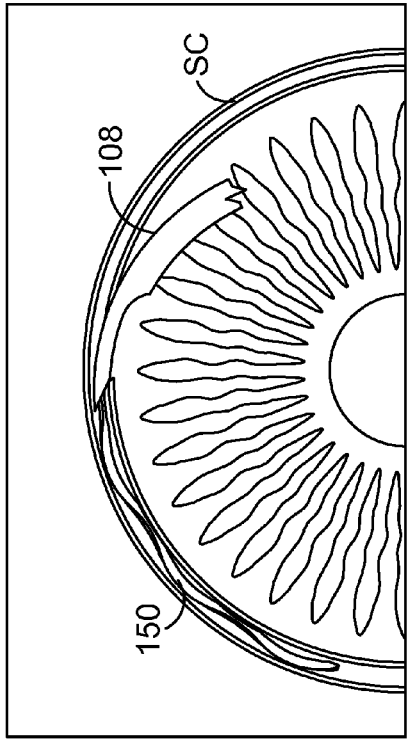

FIG. 20A-FIG. 20H are a series of stylized plan views illustrating example methods in accordance with this detailed description and associated apparatus used while performing those methods. In FIG. 20A, a distal portion of cannula 108 is shown extending through the wall of Schlemm's canal SC. In the embodiment of FIG. 20A, cannula 108 includes a sharp portion at its distal end 134 configured for cutting and/or pierced the trabecular meshwork and the wall of Schlemm's canal SC. In the embodiment of FIG. 20A, the distal end of cannula 108 has been advanced through the trabecular meshwork and the wall of Schlemm's canal SC and a passageway defined by cannula 108 has been placed in fluid communication with the lumen defined by Schlemm's canal SC.

Figure 20B:
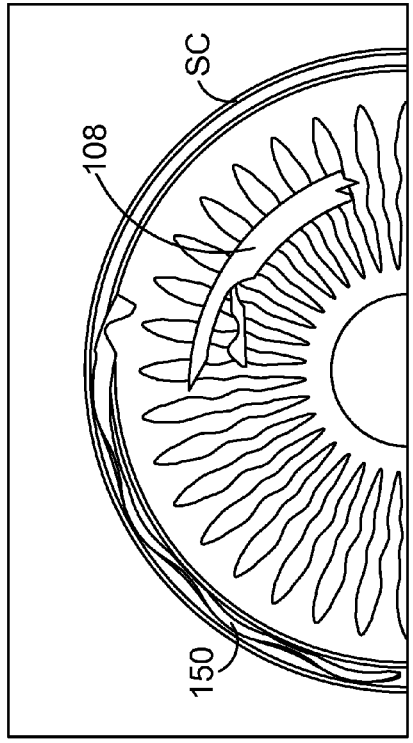

FIG. 20B is an additional stylized plan view showing cannula 108 shown in the previous figure. In the embodiment of FIG. 20B, an ocular implant 150 has been advanced out of a distal opening of cannula 108 and into Schlemm's canal SC. In FIG. 20B, a distal portion of ocular implant 150 is shown residing in a lumen defined by Schlemm's canal.

Figure 20C:
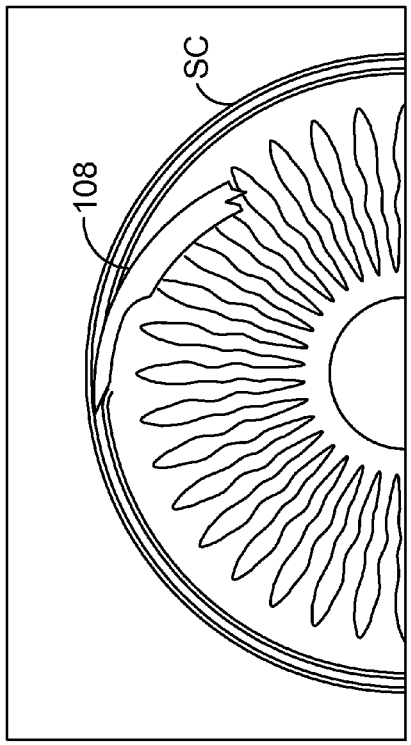

FIG. 20C is an additional stylized plan view showing ocular implant 150 and cannula 108. In the embodiment of FIG. 20C, an interlocking portion 160 of delivery tool 152 and complementary interlocking portion 162 of ocular implant 150 are both disposed near a trough portion of cannula 108. Ocular implant 150 has been advanced in a distal direction D (relative to the embodiment shown in the previous figure) so that more of ocular implant 150 is disposed inside Schlemm's canal SC. In FIG. 20C, ocular implant is shown residing in a fully deployed position. As shown in FIG. 20C, interlocking portion 160 of delivery tool 152 has disengaged from complementary interlocking portion 162 of ocular implant 150.

In the embodiment of FIG. 20C, distal opening 132 defined by cannula 108 is shaped and dimensioned so as to allow interlocking portion 160 of delivery tool 152 to extend therethrough when ocular implant 150 reaches the fully deployed position shown in FIG. 20C. When surface 161 has entered opening 132, a distal portion of delivery tool 152 is free to flex radially inward toward a curved, at-rest shape extending through distal opening 132 when ocular implant 150 reaches the fully deployed position shown in FIG. 20C to disengage from the ocular implant.

Figure 20D:
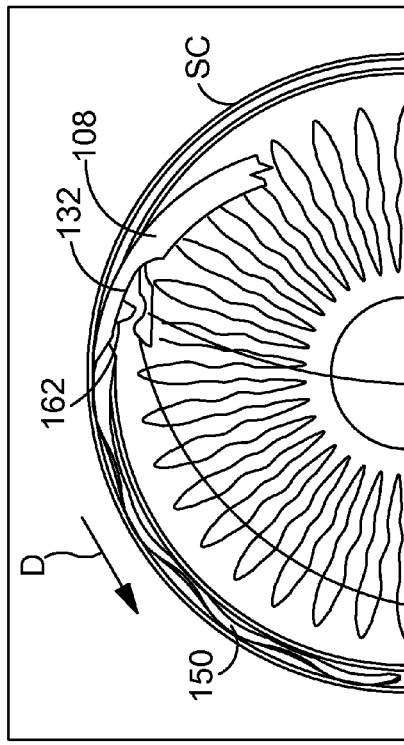

FIG. 20D is a plan view of Schlemm's canal SC after cannula 108 has been moved away from ocular implant 150. After moving cannula 108 away from ocular implant 150, a physician may visually inspect the present location of the ocular implant to determine whether that location is acceptable. If the physician determines that the present location is unacceptable, the physician may use the systems and methods described herein to recapture and reposition the ocular implant. The figures described below illustrate exemplary methods and apparatus for recapturing and repositioning the ocular implant.

In the embodiment of FIG. 20E, cannula 108 has been positioned so that the complementary interlocking portion 162 of ocular implant 150 is disposed between cannula 108 and the interlocking portion 160 of delivery tool 152. Further distal movement of cannula 108 will cause delivery tool surface 161 to re-engage with the inner wall of cannula 108, thereby moving the interlocking portion 160 of the delivery tool into re-engagement with the ocular implant. The delivery tool and ocular implant can thereafter be moved proximally, possibly together with the cannula, to reposition the implant for subsequent redeployment.

FIG. 20F is an additional stylized plan view showing ocular implant 150 and cannula 108 shown in the previous figure. By comparing FIG. 20F with the previous figure, it will be appreciated that delivery tool 152 and ocular implant 150 have been moved in a proximal direction P so that a portion of ocular implant 150 has been withdrawn from Schlemm's canal SC. In the embodiment of FIG. 20F, the complementary interlocking portion of ocular implant 150 and the interlocking portion of delivery tool 152 have both been drawn into the passageway defined by cannula 108. Also in the embodiment of FIG. 20F, the side wall of cannula 108 is holding the distal portion of delivery tool 152 in a deformed shape with the interlocking portion of delivery tool 152 engaging the complementary interlocking portion of ocular implant 150.

FIG. 20G is an additional stylized plan view showing ocular implant 150 and cannula 108 shown in the previous figure. In the embodiment of FIG. 20G, ocular implant 150 has been advanced out of a distal opening of cannula 108 and into Schlemm's canal SC. In FIG. 20G, a distal part of ocular implant 150 is shown residing in a lumen defined by Schlemm's canal. In the embodiment of FIG. 20G, interlocking portion 160 of delivery tool 152 and complementary interlocking portion 162 of ocular implant 150 are both once again located near a trough portion of cannula 108. In FIG. 20G, ocular implant is shown residing in a second fully deployed position. In the embodiment of FIG. 20G, the delivery tool 152 has once again disengaged from ocular implant 150 by permitting interlocking portion 160 of delivery tool 152 to move away from complementary interlocking portion 162 of ocular implant 150

FIG. 20H is a stylized plan view showing ocular implant 150 and Schlemm's canal SC after the cannula (seen in the previous figure) has been withdrawn leaving an inlet portion of ocular implant 150 in the anterior chamber of the eye and the remainder of ocular implant 150 in Schlemm's canal. When in place within the eye, ocular implant 150 will support the trabecular meshwork and Schlemm's canal tissue and will provide for improved communication between the anterior chamber and Schlemm's canal (via the trabecular meshwork) and between pockets or compartments along Schlemm's canal. Accordingly, the presence of ocular implant 150 in Schlemm's canal will facilitate the flow of aqueous humor out of the anterior chamber.

With reference to the figures described above, it will be appreciated that methods in accordance with the present detailed description may be used to position at least a distal portion of an implant in Schlemm's canal of an eye. In some cases, a proximal inlet portion of the ocular implant may be left in the anterior chamber. An exemplary method in accordance with the present detailed description may include the step of advancing a distal end of a cannula through a cornea of the eye so that a distal portion of the cannula is disposed in the anterior chamber of the eye. The cannula may be used to access Schlemm's canal, for example, by cutting and/or piercing the wall of Schlemm's canal with a distal portion of the cannula. A distal opening of the cannula may be placed in fluid communication with Schlemm's canal. The distal end of the ocular implant may be advanced through the distal opening of the cannula and into Schlemm's canal.

After delivering an ocular implant into Schlemm's canal, a physician may visually inspect the present location of the ocular implant to determine whether that location is acceptable. If the physician determines that the present location is unacceptable, the physician may use the systems and methods described herein to recapture and redeliver the ocular implant. Recapturing and redelivering the ocular implant may include the steps of forming a second connection between the delivery tool and the ocular implant and moving the delivery tool and the ocular implant in a proximal direction so that at least a portion of the ocular implant is withdrawn from Schlemm's canal. A distal part of the ocular implant may be advanced into Schlemm's canal while the ocular implant is coupled to the delivery tool at the second connection. The second connection may be selectively broken to release the ocular implant from the delivery system while the distal part of the ocular implant is disposed in Schlemm's canal.

Figure 21:
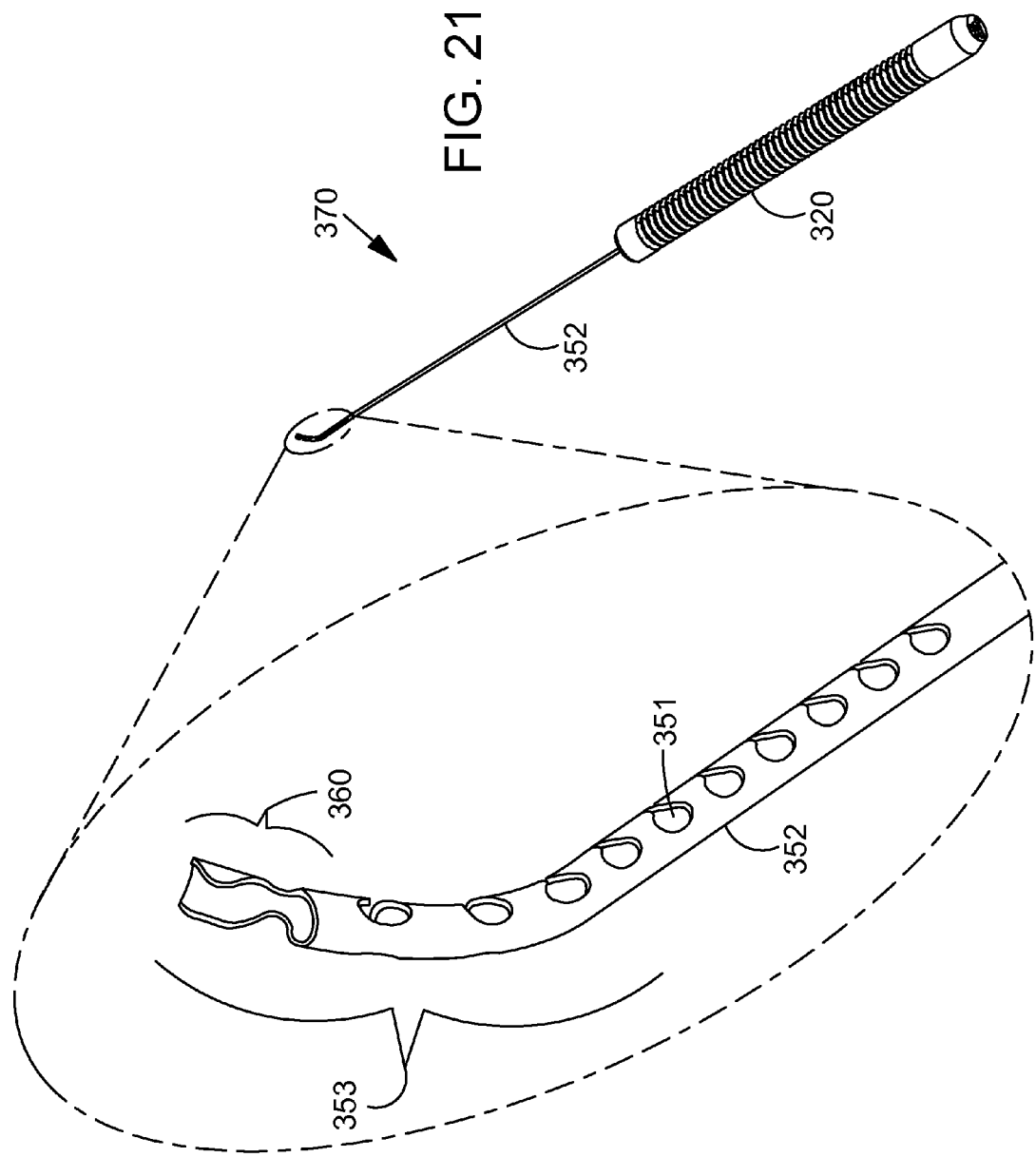
FIG. 21 is a perspective view showing a delivery tool subassembly 370 that may be part of a delivery system (e.g., the delivery system shown in FIG. 8).

FIG. 21 is a perspective view showing a delivery tool subassembly 370 that may be part of a delivery system (e.g., delivery system 100 shown in FIG. 8). Delivery tool subassembly 370 of FIG. 21 comprises a rotating rack gear 320 that is fixed to a delivery tool 352. Delivery tool 352 includes an interlocking portion 360 and a curved distal portion 353. Curved distal portion 353 of delivery tool 352 is biased to assume the curved at-rest shape shown in FIG. 21 when no external forces are acting on it. Curved distal portion 353 of delivery tool 352 may be urged to assume a straightened shape, for example, when it is disposed in a straight portion of a passageway defined by a cannula. Optional cut-outs 351 may be formed in the wall of delivery tool 352 to reduce friction during tool advancement by reducing the bending force. The cannula wall may also hold interlocking portion 360 of delivery tool 352 into engagement with a complementary interlocking portion of an ocular implant to form a mechanically interlocking connection.

FIG. 22A is a stylized plan view showing delivery tool 352 shown in the previous figure. In the embodiment of FIG. 22A, delivery tool 352 is extending into a passageway 338 defined by a cannula 308. A distal portion of cannula 308 defines a trough 354 that communicates with the passageway 338 defined by the wall of cannula 308. Trough 354 opens out the distal end of cannula 308. Trough 354 also opens into an elongate opening 332 defined by the edge 342 of the cannula wall.

In FIG. 22A, cannula 308 is illustrated in partial cross section. Interlocking portion 360 of delivery tool 352 and a complementary interlocking portion 362 of an ocular implant 350 are visible in FIG. 22A. In the embodiment of FIG. 22A, interlocking portion 360 of delivery tool 352 and complementary interlocking portion 362 of ocular implant 350 are engaging each other to form a mechanically interlocking connection such that the implant's interlocking portion 362 is proximal to the delivery tool's interlocking portion 360. The delivery tool 352 and ocular implant 350 may be selectively disengaged when interlocking portion 360 of delivery tool 352 is allowed to move away from and disengage complementary interlocking portion 362 of ocular implant 350. In the embodiment of FIG. 22, the wall of cannula 308 is preventing interlocking portion 360 of delivery tool 352 from moving away from and disengaging complementary interlocking portion 362 of ocular implant 350. A surface 363 of delivery tool 352 can be seen contacting the wall of cannula 308 at a point S in FIG. 22.

In FIG. 22A, interlocking portion 360 of delivery tool 352 is shown disposed within cannula passageway 338 at a location proximal of trough 354 and distal opening 332. In some useful embodiments, opening 332 is dimensioned and positioned such that, when the ocular implant reaches a pre-defined location along the passageway, the distal portion of delivery tool 352 will be free to move toward a curved at-rest shape. When the delivery tool assumes a curved shape, the interlocking portion of the delivery tool moves away from and disengages the complementary interlocking portion of the ocular implant. In this way, delivery tool 352 and ocular implant 350 may be selectively disengaged as delivery tool 352 is moved distally along the passageway defined by the cannula from a starting location proximal of opening 332.

FIG. 22B is an additional stylized plan view illustrating cannula 308, ocular implant 350, and delivery tool 352 shown in the previous figure. By comparing FIG. 22B with FIG. 22A, it will be appreciated that delivery tool 352 has been advanced in a distal direction D so that delivery tool 352 is extending through opening 332 and ocular implant 350 is outside of cannula passageway 338. In the embodiment of FIG. 22B, interlocking portion 360 has moved away from complementary interlocking portion 362 and ocular implant 350 and delivery tool 352 have disengaged.

Figure 23:
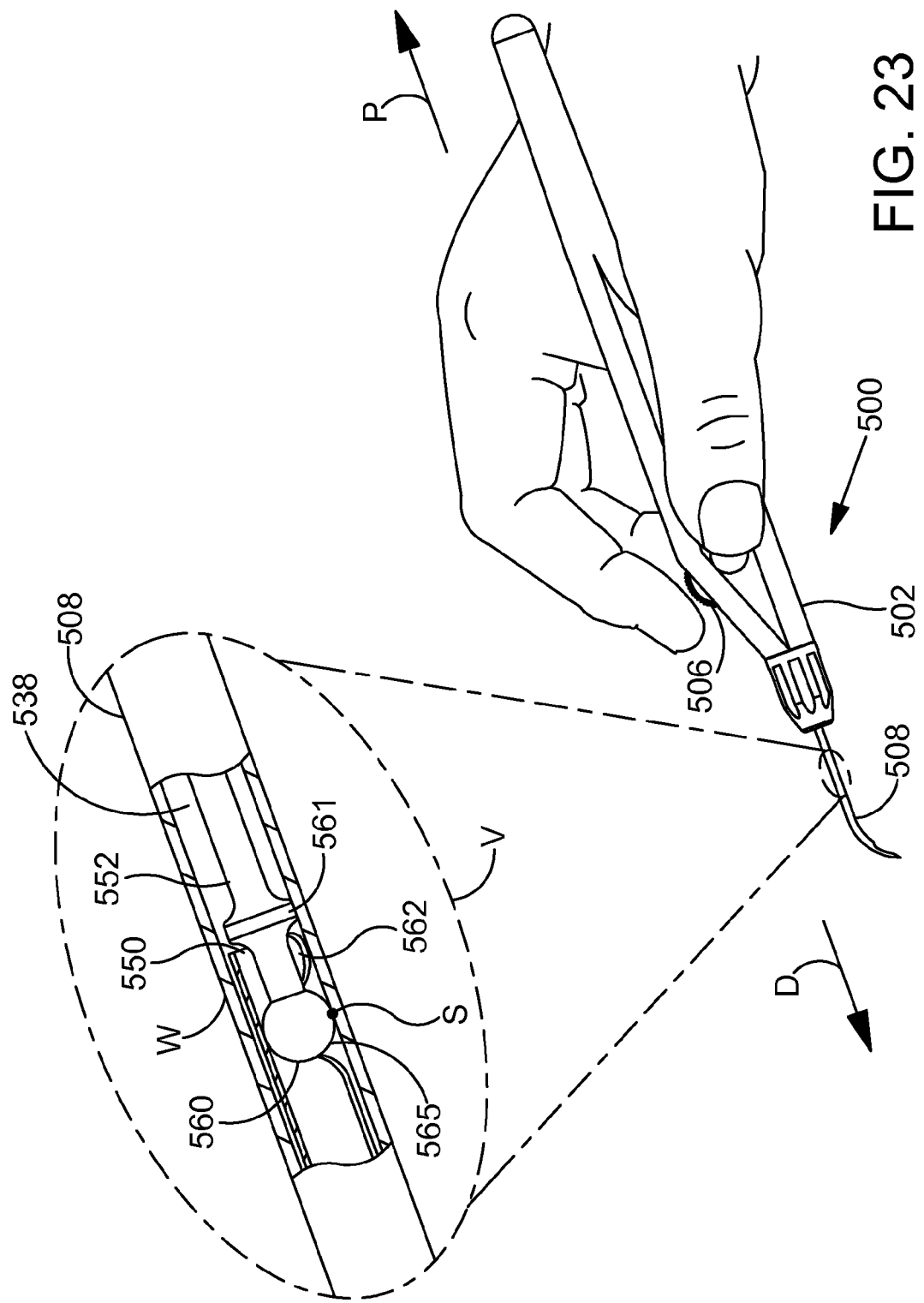
FIG. 23 is a stylized plan view showing a delivery system including an ocular implant disposed in a passageway defined by a cannula.

FIG. 23 is a stylized plan view showing a delivery system 500 including an ocular implant 550 disposed in a passageway 538 defined by a cannula 508. FIG. 23 includes an enlarged detail view V illustrating a portion of cannula 508. For purposes of illustration, a hypothetical window W is cut through the wall of cannula 508 in FIG. 23. An interlocking portion 560 of a delivery tool 552 and a complementary interlocking portion 562 of ocular implant 550 are visible through window W. In the embodiment of FIG. 23, interlocking portion 560 of delivery tool 552 and complementary interlocking portion 562 of ocular implant 550 are engaging each other to form a mechanically interlocking connection. When delivery tool 552 is confined, such as within cannula passageway 538, it can be held in mechanically interlocking engagement with ocular implant 550 so that these elements move together through passageway 538 of cannula 508. An optional ring 561 proximal to interlocking portion 560 and to the proximal end of implant 550 maintains the spacing between interlocking portion 560 and interlocking portion 562 so that they can be more easily disengaged. The wall of cannula 508 prevents interlocking portion 560 of delivery tool 552 and complementary interlocking portion 562 of ocular implant 550 from disengaging one another in the embodiment of FIG. 23. A surface 565 of delivery tool 552 can be seen contacting the wall of cannula 508 at a point S in FIG. 23.

Delivery system 500 of FIG. 23 may be used to advance ocular implant 550 into a target location in the eye of a patient. Delivery system 500 includes a housing 502 and a tracking wheel 506 that can be seen extending through the wall of housing 502 in FIG. 23. Tracking wheel 506 is part of a mechanism that is capable of advancing and retracting delivery tool 552 of delivery system 500. Rotating tracking wheel 506 will cause delivery tool 552 to move in an axial direction along a passageway 538 defined by cannula 508. The axial direction may be in a distal direction D or a proximal direction P. Ocular implant 550 moves along with delivery tool 552 as it is advanced and retracted relative to cannula 508 by the delivery system mechanism.

In the embodiment of FIG. 23, housing 502 is configured to be gripped with one hand while providing control over the axial advancement and retraction of the ocular implant via tracking wheel 506. The design of housing 502 results in an advantageous ergonomic relationship of the fingers relative to the hand. This design provides a configuration that will allow a user, such as a physician, to stabilize the device using part of the hand, while leaving the middle or index finger free move independently from the remainder of the hand. The middle or index finger is free to move independently to rotate tracking wheel 506 of delivery system 500 for advancing and/or retracting delivery tool 552.

FIG. 24A is a stylized plan view further illustrating cannula 508 shown in the previous figure. A distal portion of cannula 508 defines a trough 554 that communicates with a passageway 538 defined by the wall of cannula 508. Trough 554 opens out the distal end of cannula 508. Trough 554 also opens into an elongate opening 532 defined by the edge 542 of the cannula wall. An ocular implant 550 and a portion of a delivery tool 552 are disposed within cannula passageway 538. A distal portion of delivery tool 552 is biased to assume a curved at-rest shape when no external forces are acting on it. In the embodiment of FIG. 24A, the distal portion of delivery tool 552 is disposed in a straight portion of the cannula passageway 538 so that it is urged to assume a straightened shape.

FIG. 24B is an additional stylized plan view illustrating cannula 508, ocular implant 550, and delivery tool 552 shown in the previous figure. In FIG. 24B, delivery tool 552 is shown extending through opening 532 and ocular implant 550 is shown in a location outside of cannula passageway 538. In FIG. 24B, a gap can be seen between interlocking portion 560 of delivery tool 552 and a complementary interlocking portion 562 of ocular implant 550 in FIG. 24B. Accordingly, it will be appreciated that ocular implant 550 and delivery tool 552 have disengaged. In the embodiment of FIG. 24B, the distal portion of delivery tool 552 has flexed through distal opening 532 as it has assumed a curved shape.

Reference is now made to both FIG. 24A and FIG. 24B which may be collectively referred to as FIG. 24. In the embodiment of FIG. 24A, the distal end of delivery tool 552 is disposed within cannula passageway 538 at a location proximal of trough 554 and distal opening 532. In the embodiment of FIG. 24B, delivery tool 552 has been advanced in a distal direction D so that delivery tool 552 is extending through opening 532. Opening 532 is dimensioned and positioned such that, when the ocular implant reaches a predefined location along the passageway, the distal portion of delivery tool 552 will be free to move toward a curved at-rest shape. When the delivery tool assumes a curved shape, the interlocking portion of the delivery tool moves away from and disengages the complementary interlocking portion of the ocular implant. In this way, delivery tool 552 and ocular implant 550 may be selectively disengaged as delivery tool 552 is moved distally along passageway 538 from the position shown in FIG. 24A to the position shown in FIG. 24B.

FIG. 25A is a perspective view showing a delivery tool subassembly 770 that may be part of a delivery system (e.g., delivery system 100 shown in FIG. 8). Delivery tool subassembly 770 of FIG. 25A comprises a rotating rack gear 720 that is fixed to a delivery tool 752 formed as a flat ribbon. FIG. 25B is enlarged perspective view showing a distal portion of delivery tool 752. FIG. 25A and FIG. 25B may be collectively referred to as FIG. 25. Delivery tool 752 of FIG. 25 includes an interlocking portion 760 and a curved distal portion 753. Curved distal portion 753 of delivery tool 752 is biased to assume the curved at-rest shape shown in FIG. 25 when no external forces are acting on it. Curved distal portion 753 of delivery tool 752 may be urged to assume a straightened shape, for example, when it is disposed in a straight portion of a passageway defined by a cannula. The cannula wall may also hold interlocking portion 760 of delivery tool 752 into engagement with a complementary interlocking portion of an ocular implant to form a mechanically interlocking connection.

FIG. 26A is a stylized perspective view showing a cannula 708 having a distal portion positioned so as to extend through the wall of Schlemm's canal SC. The distal tip of cannula 708 may include a sharp portion configured for cutting and/or pierced the trabecular meshwork and the wall of Schlemm's canal so that a passageway 738 defined by the cannula can be placed in fluid communication with the lumen defined by Schlemm's canal. With the passageway of the cannula placed in fluid communication with the lumen of Schlemm's canal, an ocular implant 750 can be advanced out of the distal opening of the cannula and into Schlemm's canal. Insertion of the ocular implant into Schlemm's canal may facilitate the flow of aqueous humor out of the anterior chamber of the eye.

In FIG. 26A, delivery tool 752 is shown extending out of passageway 738 defined by a cannula 708. A surface 767 of delivery tool 752 rests against an inner wall surface of cannula 708 to keep delivery tool 752 interlocked with ocular implant 750. A distal portion of cannula 708 defines a trough 754 that communicates with passageway 738 defined by the cannula wall. Trough 754 opens out the distal end of cannula 708. Trough 754 also opens into an elongate opening 732 defined by the edge 742 of the cannula wall.

FIG. 26B is an additional perspective view showing ocular implant 750 and cannula 708 shown in the previous figure. By comparing FIG. 26B with the previous figure, it will be appreciated that ocular implant 750 and delivery tool 752 have advanced further distally so that part of delivery tool surface 767 and part of distal curved portion 753 have now passed through opening 732, thereby permitting the distal tool portion to move toward its curved at-rest shape so that the delivery tool interlocking portion 760 disengages and moves away from its complementary interlocking portion 762 on the ocular implant 750.

Reference is now made to both FIG. 26A and FIG. 26B which may be collectively referred to as FIG. 26. In the embodiment of FIG. 26, ocular implant 750 tracks along trough 754 as it is advanced distally along cannula 708. The trough opening allows the physician to monitor the progress of the implant by viewing the implant structures as they advance through the trough prior to entering Schlemm's canal. The trough opening also allows the physician to identify the position of the proximal end of the ocular implant with respect to the incision made by the cannula to access Schlemm's canal. Additionally, the trough opening allows the physician to see when the delivery tool is going to release the implant to monitor when he or she will lose the ability to retract the implant.

While exemplary embodiments of the present invention have been shown and described, modifications may be made, and it is therefore intended in the appended claims to cover all such changes and modifications which fall within the true spirit and scope of the invention.

What is claimed is:

1. A system comprising:
a cannula having a side wall defining a passageway, the cannula having a curved distal portion extending between a distal end and a proximal portion along a radius of curvature, the cannula including an opening extending through the distal end and the side wall to form a trough portion, the opening fluidly communicating with the passageway;
an ocular implant disposed inside the passageway defined by the cannula; and
a delivery tool having a distal interlocking portion engaging a complementary interlocking portion of the ocular implant to form a mechanically interlocking connection when the interlocking portion of the delivery tool is proximal to the trough portion of the cannula, the delivery tool distal interlocking portion having a curved at-rest shape having a smaller radius of curvature than the radius of curvature of the cannula distal portion, the cannula side wall preventing the delivery tool distal interlocking portion from assuming its at-rest shape when the delivery tool distal interlocking portion is proximal to the trough portion of the cannula.

2. The system of claim 1, wherein the delivery tool distal interlocking portion at-rest shape is a curve having a smaller radius of curvature than a radius of curvature of the cannula.

3. The system of claim 1, wherein the system comprises a cannula subassembly including the cannula and a delivery tool subassembly including the delivery tool, the delivery tool subassembly and the cannula subassembly engaging one another at a keyed interface, the keyed interface being configured to permit the delivery tool to slide along the passageway defined by the cannula, and the keyed interface being configured to prohibit rotation of the delivery tool subassembly relative to the cannula subassembly so that a predetermined orientation between the delivery tool and the cannula is maintained.

4. A system comprising:
a cannula having a side wall defining a passageway, the cannula including an opening extending through a distal end and the side wall to form a trough portion, the opening fluidly communicating with the passageway;
an ocular implant disposed inside the passageway defined by the cannula; and
a delivery tool having a distal interlocking portion engaging a complementary interlocking portion of the ocular implant to form a mechanically interlocking connection when the interlocking portion of the delivery tool is proximal to the trough portion of the cannula,
wherein the delivery tool subassembly includes a rotating rack gear defining a shaped hole having a predetermined shape in lateral cross-section and the cannula subassembly including a shaped portion configured to cooperate with the shaped hole of the rotating rack gear so that the delivery tool is free to slide along the passageway defined by the cannula and rotation of the delivery tool relative to the cannula is prohibited.

5. The system of claim 1 wherein the delivery tool further comprises a cannula wall engagement surface diametrically opposite the interlocking portion and a reduced diameter portion proximal to the interlocking portion.

6. The system of claim 1, wherein the mechanically interlocking connection is configured to preclude axial movement of the ocular implant relative to the delivery tool.

7. The system of claim 1, wherein the mechanically interlocking connection is configured to preclude rotation of the ocular implant relative to the delivery tool.

8. The system of claim 1, wherein the mechanically interlocking connection comprises a peak of the delivery tool that is received in a valley of the ocular implant.

9. The system of claim 1, wherein the mechanically interlocking connection comprises a peak of the ocular implant that is received in a valley of the delivery tool.

10. The system of claim 1 further comprising a motion control mechanism configured to be operated from a location outside of the eye to move the delivery tool and the ocular implant along the passageway defined by the cannula.

* * * * *